United States Patent
Rouleau et al.

(10) Patent No.: US 6,693,170 B2
(45) Date of Patent: Feb. 17, 2004

(54) ARIP4 GENE AND PROTEIN

(76) Inventors: Nathalie Rouleau, 4704 de Bordeaux, Montreal, P.Q. (CA), H2H 2A1; Anu-Maarit Moilanen, Karviaiskatu 2 J 43, Turku (FI), FIN-20720; Jorma J. Palvimo, Lumikintie 7 D 37, Helsinki (FI), FIN-00820; Olli A. Jänne, Hiiralankaari 23 B 12, Espoo (FI), FIN-02160

( * ) Notice: Subject to any disclaimer, the term of this patent is extended or adjusted under 35 U.S.C. 154(b) by 179 days.

(21) Appl. No.: 09/824,574

(22) Filed: Apr. 3, 2001

(65) Prior Publication Data

US 2003/0077800 A1 Apr. 24, 2003

(51) Int. Cl.[7] .......................... C07K 14/00; C07K 7/00; C12N 9/16
(52) U.S. Cl. ..................... 530/350; 530/300; 530/326; 530/327; 435/196
(58) Field of Search ................ 530/350, 327, 530/300, 326; 435/196

(56) References Cited

PUBLICATIONS

McDowell TL et al. Localization of a putative transcriptional regulator (ATRX) at pericentromeric heterochromatin and the short arms of acrocentric chromosomes. Proc Natl Acad Sci U S A. Nov. 23, 1999;96(24):13983–8.*

Voet et al. Biochemistry. 1990. John Wiley & Sons, Inc. pp. 126–128 and 228–234.*

Abstract P1433, presented at 11th International Congress of Endocrinology, Sydney, Australia (Oct. 29–Nov. 2, 2000.*

Abstract P1433, presented at 11th International Congress of Endocrinology, Sydney, Australia (Oct. 29–Nov. 2, 2000).

"Stable Expression of Novel Androgen Receptor Coregulator ARIP4 in HeLa Cells," poster presented at 11th International Congress of Endicrinology, Sydney, Australia (Oct. 29–Nov. 2, 2000).

* cited by examiner

*Primary Examiner*—Yvonne Eyler
*Assistant Examiner*—Joseph F. Murphy
(74) *Attorney, Agent, or Firm*—Rothwell, Figg, Ernst & Manbeck, p.c.

(57) ABSTRACT

This invention relates to a novel nuclear protein which interacts with the androgen receptor in vivo and in vitro, and which also possesses ATPase activity. The invention concerns also mRNA and DNA sequences encoding said protein.

4 Claims, 7 Drawing Sheets

A

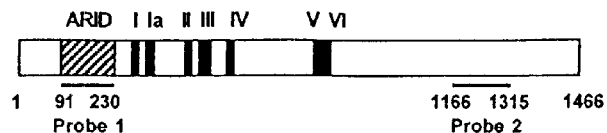

B

```
  1 MSDESASGSD PDLDPDVELE DEEEEEEEEE VAVEEHDRDD EEGLLDDTSL EGMCGTEHAQ
                                               ┌──────NLS──────┐
 61 LGEDGQRPPR CTSTTSSQSE PSEQLRHQGK ILASEDPKKK RAOKPSHMRR NIRKLLREDQ
121 LEPVTKAAQQ EELERRKRLE QQRKEYAAPI PTVPLEFLPE EIVLRASDGP OLPPRYLAOE
181 YICLDSSSGS EDEKSSRDEV IELSSGEEDT LHIVDSSESV SEEDEEEEKG GTHVNDALNQ
241 HDALGRVLVN LNHPPEEENV FLAPQLARAV KPHQIGGIRF LYDNLVESLE RFKTSSGFGC
            ┌─────I─────┐                       ┌────Ia────┐
301 ILAHSMGLGK TLQVISFIDV LFRHTPAKTV LAIVPVNTLQ NWLAEFNMWL PAPEALPADS
                                                          ┌─────
361 KPEEVQPRFF KVHILNDEHK TVASRAKVTA DWVSEGGVLL MGYEMYRLLT LKKSLATSRP
    ─NLS─┐                          ┌─────II─────┐
421 KKTKKRSHPV IIDLDEEDRQ QEFRREFEKA LCRPGPDVVI CDEGHRIKNC QASTSQALKN
    ┌──III──┐
481 IRSRRRVVLT GYPLQNNLIE YWCMVDFVRP DFLGTRQEFS NMFERPILNG QCIDSTPQDV
541 RLMRYRSHVL HSLLEGFVQR RGHTVLKIHL PAKEENVILV RLSQIQRDLY TQFMDRFRDC
601 GTSGWLGLNP LKAFCVCCKI WNHPDVLYEA LQKENLANEQ DLDVEELGSA GTSARCPPHG
661 TKVKGEDSAL PSSMGEATNS KFLQGVGFNP FQERGNNIVT YEWAKELLTN YQTGVLENSP
                                            ┌─────IV─────┐
721 KMVLLFHLIE ESVKLGDKIL VFSQSLSTLA LIEEFLGKRD MPCLPGAEGQ GTQKWVRNVS
                                               ┌─────V─────┐
781 YFRLDGSTPA FERERLINQF NDPSNLTTWL FLLSTRAGCL GVNLIGANRV VVFDASWNPC
    ─────────VI─────────┐
841 HDAQAVCRVY RYGQKKPCHI YRLVADYTLE KKIYDRQISK QGMSDRVVDD LNPMLNFTRK
901 EVENLLHFVE KEPAPQTSLD IKGIKESVLQ LACLKYPHLI TKEPFEHESL LLNRKDHKLT
961 KAEKKAAKKS YEEDKRTSVP YTRPSYAQYY PASDQSLTSI PAFSQRNWQP TLKGDEKPVA
1021 SVRPVQSTPI PMMPRHVPLS GGVSSASSTN TSMNFPINYL QRAGVLVQKV VTTTDIVIPG
1081 LNSSTDVQAR INAGESIHII RGTKGTYIRT SDGRIFAVRA TGKPKAPEDG RMAASGSQGP
1141 SLASTSNGRH SASSPKAPDP EGLARPVSPD SPEIISELQQ YADVAAARES RQSSPSISAA
                                                         ┌─────
1201 LPGPPGQLMD NSTIPGTALG TEPCLGGHCL NSSLLVTGQP SGGRHPVLDL RGHKRKLATP
     ─NLS─────┐
1261 SVTQESIRRR SRKGHLPAPV QPYEHGYPVS GGFAMPPVSL NHNLTTPFTS QAGENSLFMG
1321 SNPSYYQLSN LLADARLVFP VTTDPLVPAG PVSSSSTATS VTASNPSFML NPSVPGMLPS
1381 YSLPFSQPLL SEPRMFAPFP SPGLPSNLSR GVSVYPGYMS PHAGYPAGGL LRSQVPPFDS
1441 HEVAEVGFSS NDDEDKDDDV IEVTGK
```

C

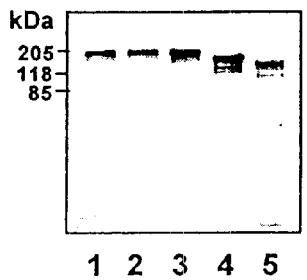

D

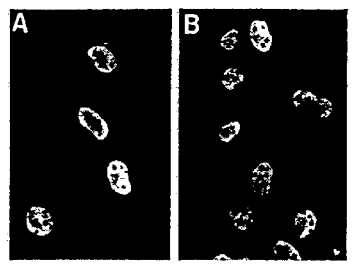

ARIP4 GENE AND PROTEIN

FIELD OF THE INVENTION

This invention relates to a novel nuclear protein which interacts with the androgen receptor in vivo and in vitro, and which also possesses ATPase activity. The invention concerns also mRNA and DNA sequences encoding said protein.

BACKGROUND OF THE INVENTION

The publications and other materials used herein to illuminate the background of the invention, and in particular, cases to provide additional details respecting the practice, are incorporated by reference.

The androgen receptor (AR) belongs to the superfamily of nuclear receptors that are ligand-activated transcription factors capable of regulating transcription of genes containing appropriate response elements, usually within or around the proximal promoter regions (Quigley et al., 1995; Beato et al., 1995; Perlmann and Evans, 1997). After hormone binding, the receptors associate with their cognate DNA motifs and modulate transcription initiation. Nuclear receptors may interact directly with the basal transcription factors associated with RNA polymerase II, such as TFIIB (Blanco et al., 1995; Hadzic et al. 1995; Ing et al., 1992) and TFIIF (McEwan and Gustafsson, 1997), or elicit their actions indirectly via auxiliary regulatory proteins, called coactivators and corepressors (Torchia et al., 1998; Freedman, 1999; McKenna et al., 1999).

In the nucleus, the DNA is folded into a tight chromatin structure that often renders important regulatory sequences inaccessible for sequence-specific transcription factors, including steroid receptors (Kingston et al., 1996). As a consequence, different chromatin remodeling complexes are required to counteract this repressive effect (Björklund et al., 1999; Lemon and Freedman, 1999; Kingston and Narlikar, 1999). Yeast SWI/SNF was the first complex shown to facilitate the function of gene regulatory proteins in a chromatin environment (Hirschhorn et al., 1992). Mammalian (hSWI/SNF, NURD, RSF), Drosophila (NURF, CHRAC, ACF) and yeast (RSC) homologs of this complex have subsequently been characterized (Kwon et al., 1994; Xue et al., 1998; LeRoy et al., 1998; Mizuguchi et al., 1997; Varga-Weisz et al., 1997; Ito et al., 1999; Tsuchiya et al., 1998). In the yeast, mutation in the components of the SWI/SNF complex results in reduced glucocorticoid (GR) and estrogen receptor (ER) activity, indicating the importance of an intact remodeling complex for steroid receptor activity (Yoshinaga et al., 1992). In addition, co-expression of GR and hbrm (a component of the hSWI/SNF complex) in cells depleted of hbrm restores the GR-dependent transcription (Muchardt and Yaniv, 1993).

The yeast SWI2/SNF2 protein was first described as the subunit responsible for the ATPase activity of the SWI/SNF complex (Khavari et al., 1993; Laurent et al., 1993; Cote et al., 1994). SWI2/SNF2 is the founding member of the family of SNF2-like proteins that share in common a 600-amino-acid-long conserved domain (the Snf2 domain) surrounded by non-conserved regions. The SNF2-like family comprises over 100 members (Eisen et al., 1995), and most of these proteins have no known biological function. However, those members that have been shown to possess well-defined functions all play distinct roles in DNA processing activities, such as replication, repair and/or transcription (Pazin and Kadonaga, 1997; Kingston and Narlikar, 1999). The Snf2 domain contains seven so-called helicase motifs and a consensus region for binding and hydrolysis of ATP. While no helicase activity has experimentally been demonstrated for any of the SNF2-like proteins, the importance of the ATPase activity is well established for many family members (Kingston and Narlikar, 1999). Phylogenetic analysis by Eisen et al. (1995) suggested that the non-conserved regions surrounding the Snf2 domain could be responsible for targeting the ATPase activity to specific compartments of cells.

SUMMARY OF THE INVENTION

According to one embodiment, this invention concerns an isolated protein being able to interact with the androgen receptor and having ATPase activity, said protein comprising the sequence of 1466 amino acids as shown in FIG. 1B, or a part thereof having similar biological activity. The protein sequence is also set forth in SEQ ID NO:2 and in GenBank Accession No. AJ132389.

According to another embodiment, the invention concerns a DNA sequence encoding a protein being able to interact with the androgen receptor and having ATPase activity, said protein comprising the sequence of 1466 amino acids as shown in FIG. 1B, or a part thereof having similar biological activity. The nucleotide sequence is set forth in SEQ ID NO:12 and in GenBank Accession No. AJ132389.

According to a third embodiment, the invention concerns an mRNA sequence encoding a protein being able to interact with the androgen receptor and having ATPase activity, said protein comprising the sequence of 1466 amino acids as shown in FIG. 1B, or a part thereof having similar biological activity.

BRIEF DESCRIPTION OF THE DRAWINGS

FIG. 1. Schematic structure, amino acid sequence, and nuclear localization of ARIP 4. (A) Functional domains of ARIP4 include the androgen receptor interaction domain (ARID) and the regions predicted to encompass ATPase/helicase activity (regions I through VI). The positions of cDNA probes used for library screenings are also shown. (B) ARIP4 amino acid sequence, SEQ ID NO: 2, predicted from the cDNA sequence. The putative functional units are depicted: NLS, nuclear localization signal; numbers I, Ia, and II–IV refer to the corresponding ATPase/helicase motifs. ARID, as predicted on the basis of the yeast two-hybrid screening results, is shown in italics and underlined, and the residues potentially important for ATPase activity are boxed. The sequence is deposited into GenBank with accession number AJ132389. (C) Immunoblot analysis of wild-type and mutated ARIP4 proteins. COS-1 cells were transfected with expression vectors encoding FLAG-tagged ARIP4 (lane 1), ARIP4K310A (lane 2), ARIP4DE462AA (lane 3), ARIP4Δ1–280 (lane 4), and ARIP4Δ1315–1466 (lane 5), and the cell extract resolved by SDS-PAGE followed by immunoblotting with a polyclonal anti-ARIP4 antibody (K7991). Each lane contains 10 μg of cell protein. Identical bands were detected with M2 monoclonal anti-FLAG antibody (data not shown). (D) Localization of ARIP4 in transfected cells. COS-1 cells grown on glass coverslips on 10-cm plastic plates were transfected with 1 μg of pFLAG-ARIP4 as described in Experimental Procedures. The cells were fixed, permeablized, and ARIP4 antigen visualized using either anti-FLAG M2 monoclonal antibody (A) or anti-ARIP4 antiserum (K7991) raised in rabbits against the 280 most C-terminal amino acid residues of ARIP4 (B).

FIG. 2. Homology of the SNF2 domain of ARIP4 with that of some other members of the SNF2-like protein family.

The numbers in parentheses depict the first and last amino acid taken for comparison in each case; the regions were as follows: SNF2 (amino acids 786–1223 of SEQ ID NO:3); BRG1 (amino acids 774–1218 of SEQ ID NO:4); Mot1 (amino acids 1293–1770 of SEQ ID NO:5); RAD54 (amino acids 176–635 of SEQ ID NO:6); ARIP4 (amino acids 298–877 of SEQ ID NO:2); and ATRX (amino acids 1574–2162 of SEQ ID NO:7). The regions that include the seven-consensus helicase motifs (I, Ia, and II–VI) are depicted by a line above the sequence. Shaded amino acids are similar in at least three of the proteins compared. The following amino acid groups are considered to be similar: L, V, I, and M; F, Y, and W; S, T, A, P, and G; K, R, and H; and E, D, Q, and N. The sequence information is from Khavari et al. (1993); Laurent and Carlson (1992); Emery et al. (1991); Davis et al. (1992); Picketts et al. (1996).

Figure 3:
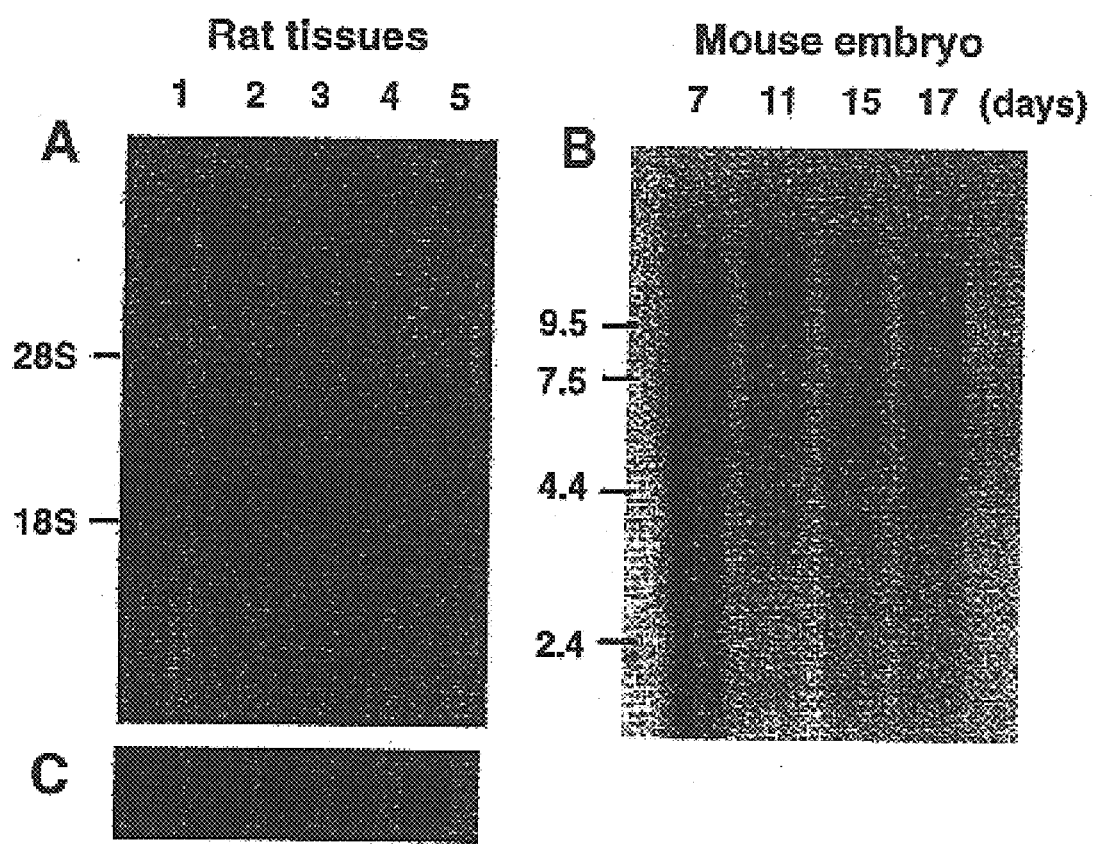

FIG. 3. Expression of ARIP4 mRNA in some adult rat tissues (A) and in mouse embryo (B). ARIP4 mRNA was detected by Northern blot analysis using a $^{32}$P-labeled ARIP4 cDNA probe corresponding to the AR interaction domain. Poly(A)+ RNA samples (5 µg/lane) originated from the following rat tissues: 1, testis; 2, prostate; 3, liver; 4, kidney; and 5, brain. Panel C shows hybridization of the rat RNA samples to a γ-actin cDNA probe.

Figure 4:
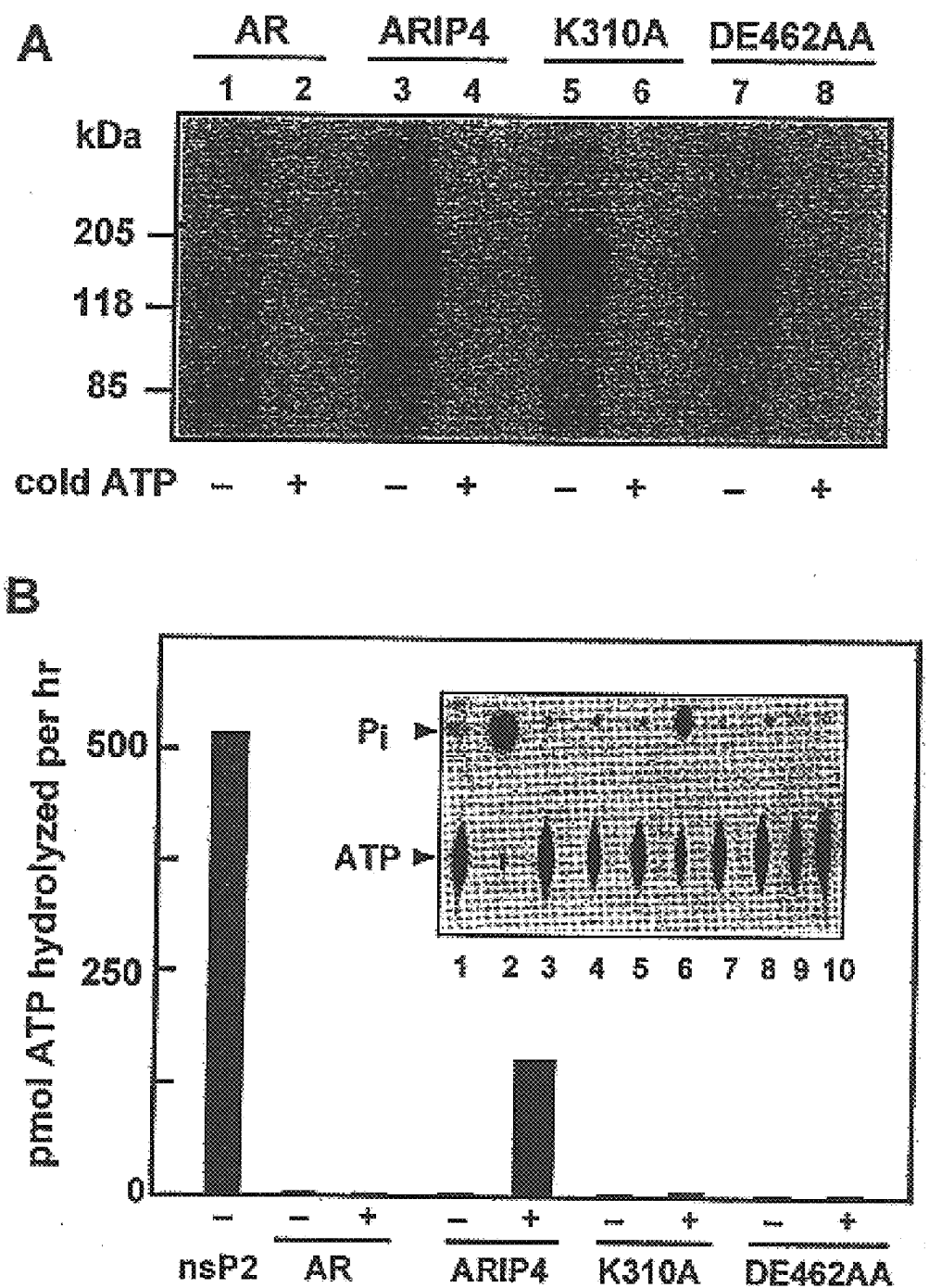

FIG. 4. Affinity-labeling with 8-azido-[γ-$^{32}$P]ATP and ATPase activity of ARIP4. (A) COS-1 cells were transfected with plasmids encoding the following FLAG-tagged proteins: AR (lanes 1 and 2); ARIP4 (lanes 3 and 4); ARIP4K310A (K310A, lanes 5 and 6); and ARIP4DE462AA (DE462AA, lanes 7 and 8). Proteins were purified by immunoadsorption onto anti-FLAG antibody matrix and affinity-labeled with 8-azido-[γ-$^{32}$P]ATP as described in Experimental Procedures. [$^{32}$P]ATP-labeled proteins were resolved by SDS-PAGE and visualized by autoradiography. The specificity of labeling was assessed by the inclusion of 1,000-fold molar excess of non-radioactive ATP during affinity labeling (lanes 2, 4, 6, and 8). The amounts of AR as well as wild-type and mutant ARIP4 proteins in each lane were similar, as judged by immunoblot analysis (not shown). (B) COS-1 cells were transfected with plasmids encoding FLAG-tagged AR, ARIP4, ARIP4K310A, and ARIP4DE462AA, and the cell extracts were immunopurified by anti-FLAG affinity matrix. The proteins eluted from the resin with FLAG peptide were subjected to ATPase assay with [γ-$^{32}$P]ATP as the substrate. Semliki forest virus nonstructural protein 2 (nsP2) was included as the positive control, and the amount of ATP hydrolyzed was calculated on the basis of its specific activity (91 pmol $^{32}$P$_i$ released/pmol protein×min$^{-1}$). The assays were performed in the absence (−) and presence (+) of 1 µg of ds-DNA as depicted. The inset shows the autoradiogram of the thin-layer plate used to resolve $^{32}$P$_i$ from [$^{32}$P]ATP. The lanes contained the following samples: 1, blank; 2, nsP2; 3 and 4, AR±ds-DNA; 5 and 6, ARIP4±ds-DNA; 7 and 8, ARIP4K310A±ds-DNA; and 9 and 10, ARIP4DE462AA±ds-DNA. The spots corresponding to $^{32}$P$_i$ and [$^{32}$P]ATP are depicted.

Figure 5:
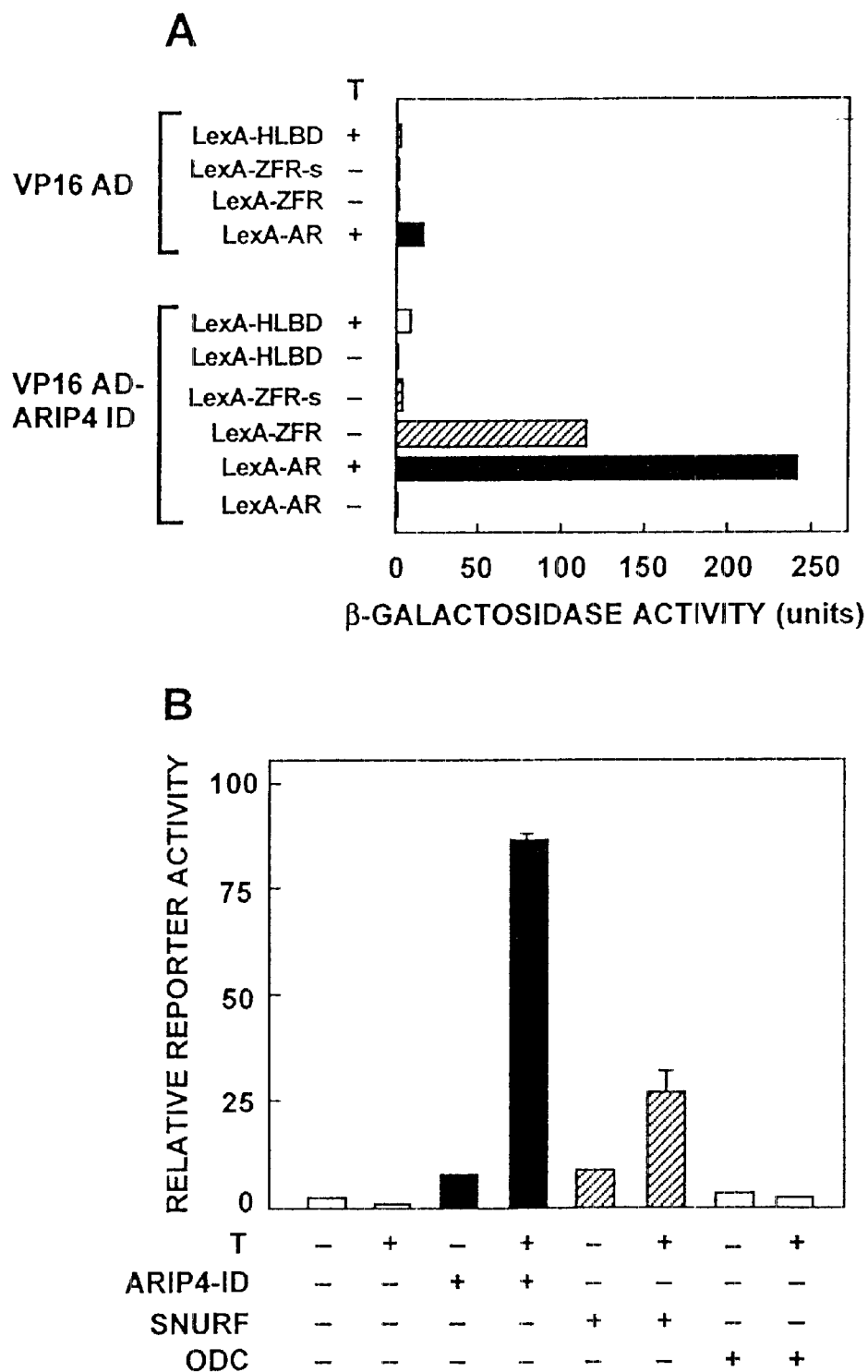

FIG. 5. ARIP4 interacts with AR and in yeast and mammalian cells. (A) The yeast two-hybrid assay. Plasmids expressing different LexA fusion proteins [LexA-AR, LexA-ZFR (amino acids 554–644 of AR), LexA-ZFR-s (amino acids 554–623 of AR), LexA-HLBD (amino acids 624–919 of AR)] were used to cotransform into *S. cerevisiae* L40 strain with plasmids expressing VP16 AD or VP16 AD fused to ARIP4 (amino acids 86–227) (VP16 AD-ARIP4 ID). Transformants were grown in the presence (+) or absence (−) of 50 nM testosterone (T) as depicted. β-Galactosidase activity in extracts of liquid culture is shown, and each bar gives the average of three independent yeast transformants. (B) Interaction of ARIP4 with AR in mammalian cells. CV-1 cells were transfected using the FuGene reagent with a reporter plasmid pG5LUC (150 ng), 30 ng of rat AR (amino acids 3–902) fused to the DBD of Gal4 (Gal4-AR), and 30 ng of the indicated VP16 AD fusion proteins depicted by the + signs. The proteins fused to VP16 AD were ARIP4-ID (ARIP4 amino acids 86–227), SNURF (SNURF residues 20–177), and human ODC. Testosterone (T, 100 nM) was present in the culture medium as indicated. Each bar corresponds to mean±SEM values of at least 3 independent experiments, and the values were calculated relative to that of Gal-AR in the presence of androgen and VP16 AD alone (=1).

Figure 6:
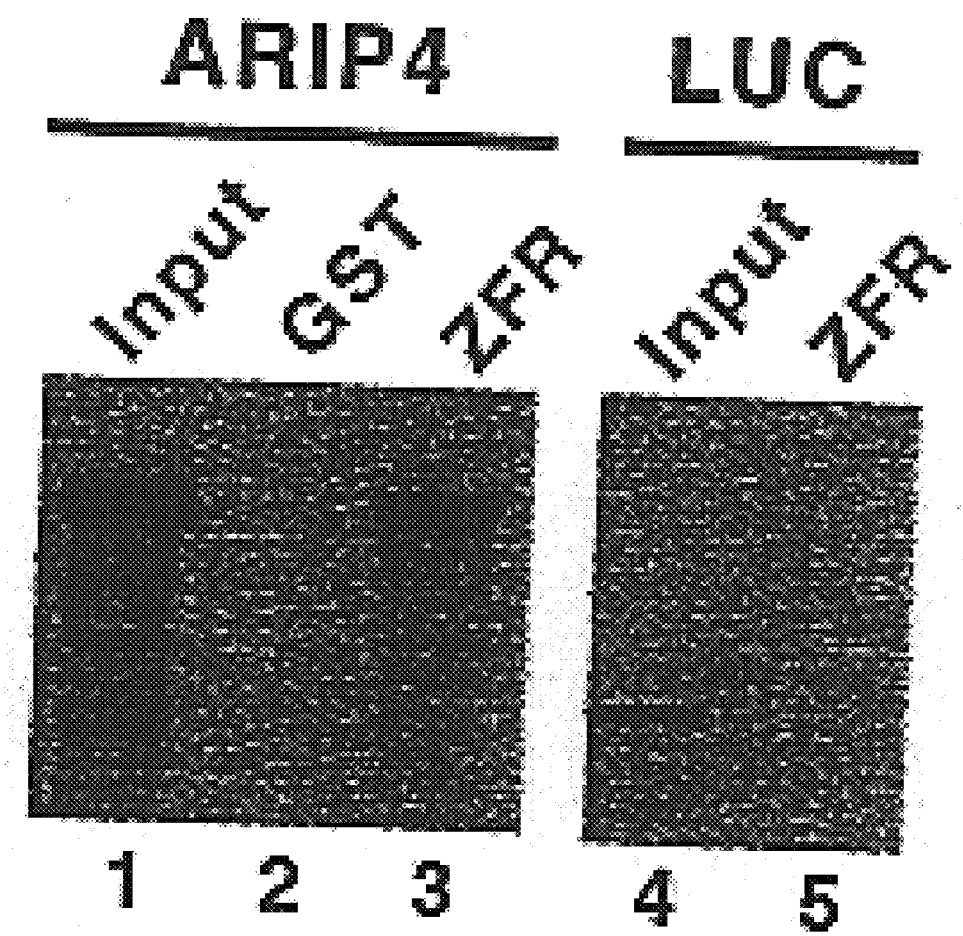

FIG. 6. In vitro interaction of ARIP4 with the zinc finger region of the androgen receptor (AR ZFR). Full-length ARIP4 or luciferase (LUC), labeled with [$^{35}$S]methionine by translation in vitro using reticulocyte lysate, was incubated with glutathione-Sepharose matrix alone (GST) or with the matrix containing adsorbed GST-AR ZFR fusion protein (ZFR). After washing of the matrix, the bound proteins were released by boiling in the electrophoresis sample buffer and resolved by SDS-PAGE and visualized by fluorography. Lanes 1 and 4 represent 5% of the amount of [$^{35}$S] methionine-labeled ARIP4 or LUC, respectively, incubated with the matrix.

Figure 7:
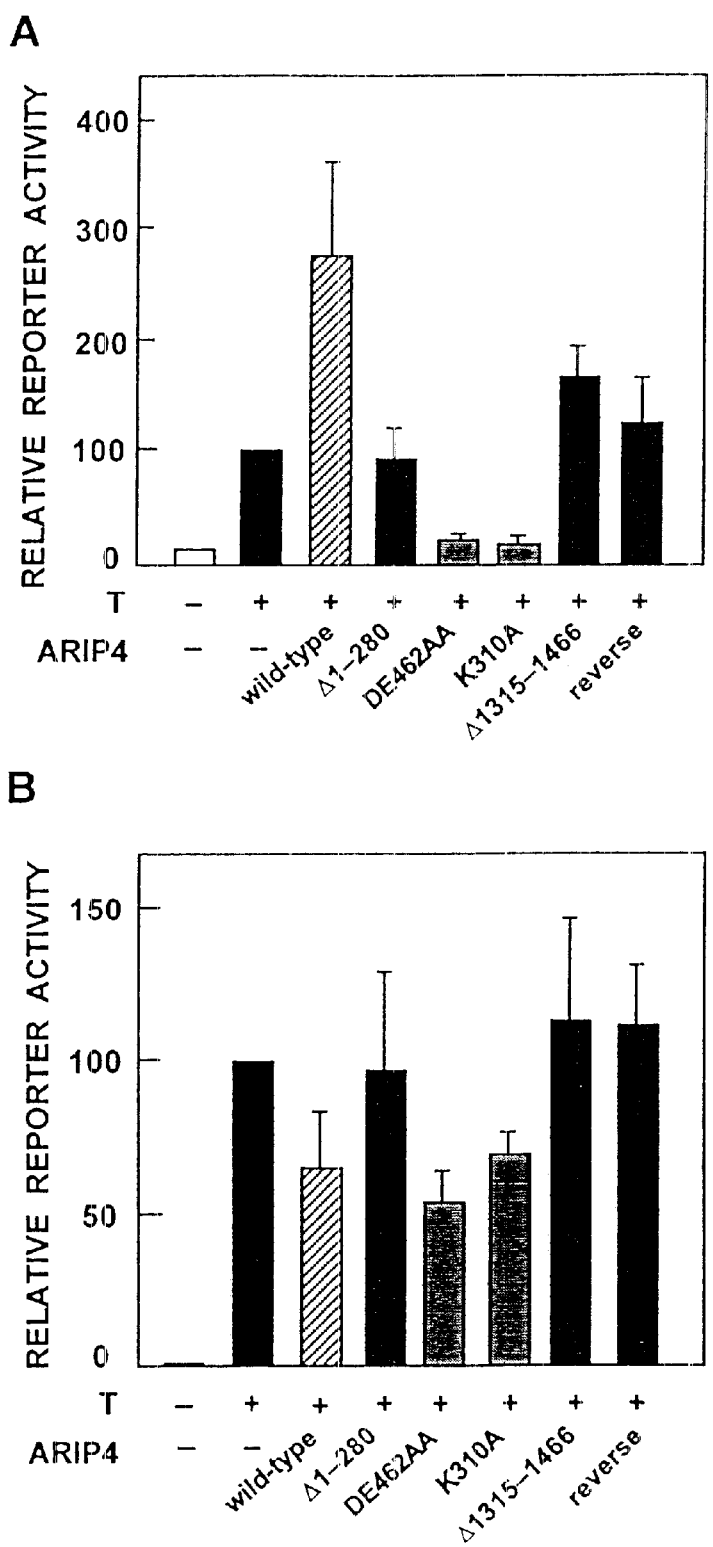

FIG. 7. Effect of ectopic ARIP4 expression on AR-dependent transactivation. (A) COS-1 cells were transfected using the FuGene reagent with 150 ng of ARE$_4$-tk-LUC, 20 ng of pSG-rAR and 30 ng of wild-type ARIP4 or ARIP4 mutants as indicated. Testosterone (T, 100 nM) was added 24 hr after transfection as depicted by the + signs, and the cells were harvested 24 hr later. The values are normalized to cell protein content and expressed relative to that of AR in the presence of androgen without ARIP4 expression plasmids (=100), and each bar represents mean±SEM values of at least 3 independent experiments. (B) COS-1 cells were transfected as in panel A, except that 150 ng of pPB(−285/+32)-LUC was used as the reporter construct. The values (mean±SEM, n=3) are normalized and expressed as in panel A. The amount of wild-type ARIP4 expression vector used (30 ng) produced a response that was 30–50% of maximal.

DETAILED DESCRIPTION OF THE INVENTION

Nuclear receptors, including the androgen receptor (AR), regulate target cell transcription through interaction with auxiliary proteins to modify chromatin structure. We, the inventors of the present invention, have identified and characterized a novel ATPase/helicase-like protein that belongs to the SWI2-like family of proteins. The protein, termed ARIP4 (for androgen receptor-interacting protein 4), interacts with AR in vivo and in vitro, and it modulates ligand-dependent transactivation properties of the receptor in a promoter-specific manner. With regard to the Snf2 domain, the closest homolog of ARIP4 is the ATRX protein. ARIP4 is a nuclear protein and comprises 1466 amino acids. It interacts with AR in vitro and in cultured yeast and mammalian cells. ARIP4 can be labeled with 8-azido-[γ-$^{32}$P]ATP and possesses DNA-dependent ATPase activity. In transient co-transfection assays, ARIP4 modulates AR function in a promoter-dependent fashion; it enhances AR activity on minimal promoters, but represses AR-mediated activation of more complex promoters. We also demonstrate that ARIP4 mutants incapable of ATP hydrolysis not only loose the ability to modulate transcriptional activity of AR but also behave as trans-dominant negative regulators of AR function.

This invention concerns especially the protein having the sequence of 1466 amino acids as shown in FIG. 1B and SEQ ID NO:2, a protein comprising the amino acids 91 to 230, a protein comprising the regions I, Ia, II, III, IV, V and VI, and a protein comprising the amino acids 301 to 874, all shown in FIG. 1B. The invention also concerns the mRNA, DNA and cDNA sequences encoding the aforementioned proteins.

The invention will be illuminated by the following non-restrictive Experimental Section.

EXPERIMENTAL SECTION

Experimental Procedures

Materials

[$\alpha$-$^{32}$P]dCTP, [$\gamma$-$^{32}$P]ATP, and [$^{35}$S]methionine were purchased from Amersham Pharmacia Biotech. 8-Azido-[$\gamma$-$^{32}$P] ATP was a product from ICN and M2 anti-FLAG antibody from Eastman Kodak. pARE$_4$-tk-LUC, pARE$_2$-TATA-LUC, pPB(−285/+32)-LUC, pSG5rAR, pcDNA3.1-FLAG-AR and Gal4-AR, VP16 activation domain (AD) fusion to SNURF have been described (Palvimo et al., 1996; Aarnisalo et al., 1998; Moilanen at al. 1998b). The yeast two-hybrid vectors were kindly provided by Dr. Stanley M. Hollenberg (Vollum Institute, Oregon Health Sciences Center, Portland, Oreg.), and the pLexA fusion proteins have been described previously (Moilanen at al., 1998b). pCMVβ and mouse E11.5 λgt11 cDNA library were purchased from CLONTECH. Ni-NTA resin and pQE-31 vector were purchased from Qiagen (Hilden, Germany).

Yeast Two-hybrid Screening

Partial sequence of ARIP4 was identified by the yeast two-hybrid assay as described by Moilanen et al. (1998b). Briefly, the human AR zinc-finger region (ZFR) containing the first 20 hinge region residues was fused to the LexA and used as a bait to screen a size selected mouse E10.5 cDNA library fused to VP16 activation domain (a gift from Dr. S. M. Hollenberg). The positive clones were tested against several control plasmids, such as pLex-a, pLex-lamin, and pLex-WT1ZF (WT1ZF, the zinc-finger region of the Wilms tumor gene product), to eliminate the false positive clones.

cDNA Cloning and Characterization

ARIP4 cDNA clones isolated in the yeast two-hybrid screen were 400–500 nt long. To isolate the full-length ARIP4 cDNA, mouse E11.5 λgt11 cDNA library was screened with $^{32}$P-labeled ARIP4 cDNA corresponding to amino acids 91–230 (FIG. 1A, probe 1) using standard hybridization conditions (Asubel et al., 1997). The longest insert was ~4.0 kb in length; it was subcloned into the Eco RI site of pBluescript II S/K to yield pBS46. The most 3'-end of this ARIP4 cDNA was cleaved with Eag I and Eco RI and used as a probe to screen again the E11.5 λgt11 cDNA library. The phage clone extending 3' from pBS46 was isolated, cleaved with Eco RI and subcloned into pBluescript II S/K to yield pBS56 and pBS57. The former (pBS56) was colinear with the ARIP4 cDNA insert in pBS46 and the latter continued 3' from pBS56.

Plasmid Constructions

To generate full-length FLAG-tagged ARIP4 (pFLAG-ARIP4), the sequences in pBS46 and pBS56 were assembled together. An in-frame Eco RI site was inserted by PCR in front of the first ATG codon in pBS46. The resulting cDNA was digested Eco RI and cloned into pCMV-FLAG-2 vector (Eastman Kodak) to generate pFLAG-ARIP4 containing amino acids 1–1315. pBS56 was then digested with Sma I/Eco RI to yield a fragment containing the rest of the protein coding region (residues 1205–1466) plus ~500 nt of the 3'-untranslated region of ARIP4 mRNA. This Sma I/Eco RI fragment was inserted into pFLAG-ARIP4(1–1315) that was linearized by a partial Sma I/Eco RI digestion to yield full-length pFLAG-ARIP4. To assemble ARIP4Δ1–280, a fragment corresponding to ARIP4 residues 281–620 was first subcloned into the Eco RI/Bgl II site of pCMV-FLAG-2. Then, ARIP4 cDNA, subcloned into the Hind III/Xba I site of pBL5CAT, was digested with Bgl II and the cleaved fragment inserted into the Bgl II site of pFLAG-ARIP4 (281–620) to yield pFLAG-ARIP4Δ1–280. The Quick-Change Site-Directed Mutagenesis Kit (Stratagene) was used to mutate ARIP4 sequence. K310, D462 and E463 were converted to Ala residues to yield pARIP4K310A and pARIP4DE462AA expression vectors, respectively. The mammalian two-hybrid vector was constructed by fusing the AR interaction domain of ARIP4 (ARID, residues 91–230) in-frame to pVP16 (CLONTECH). Human ornithine decarboxylase (ODC) cDNA was cloned between the Eco RI and Sal I sites of pVP16 to express VP16-ODC fusion protein.

Purification of the C-terminal Fragment of ARIP4 for Raising Antibodies

A 1.3-kb Sac I-Pst I cDNA fragment of ARIP4 corresponding to nt 3773–5071 was subcloned into the Sac I/Pst I site of pQE-31 (Qiagen). This fragment encodes the very C-terminal 280 amino acids of ARIP4 fused to an N-terminal His-tag. The protein was expressed in E. coli (strain JM109) and extracted from a 250-ml bacterial culture by suspension in 10 ml of buffer containing 8 M urea, 0.1 M sodium phosphate, 0.01 M Tris-HCl (pH 8.0), 0.5 mM PMSF, and 10 µg/ml aprotinin and incubation at 22° C. for 1 hr. The lysate was centrifuged at 15000 rpm for 10 min, the supernatant mixed with 2.5 ml of Ni$^{2+}$-agarose equilibrated with a buffer containing 8 M urea, 0.1 M sodium phosphate, and 0.01 M Tris-HCl (pH 6.3), and the slurry rotated for 1 hr at 22° C. The resin was washed 3 times with 10 vol of equilibration buffer, and the His-tagged proteins were released by elution with 2 ml of buffer containing 100 mM EDTA, 8 M urea, 0.1 M sodium phosphate, and 0.01 M Tris-HCl (pH 6.3). The eluted protein was ~30 kDa in size and 95% pure, as judged by SDS-PAGE. Prior to being used for immunization, urea was removed by step-wise dialysis against phosphate-buffered saline. Fifty µg of protein was used to immunize rabbits.

Cell Culture and Transfections

COS-1 cells were maintained in Dulbecco's minimal essential medium containing penicillin and streptomycin (each 25 U/ml), and 10% (vol/vol) fetal bovine serum (FBS). Transfections for transactivation assays (~3×10$^4$ cells) were performed with the FuGene reagent (Roche Molecular Biochemicals) with 150 ng of an appropriate reporter vector and the amounts of plasmids depicted in the figure legends. pCMVβ was included to monitor transfection efficiency. At 18 hr post-transfection, the medium was changed to one containing charcoal-stripped 2% (vol/vol) FBS and 100 nM testosterone or vehicle. CV-1 cells transfected with the FuGene reagent were used in the mammalian two-hybrid experiments. For affinity-labeling with 8-azido-[$\gamma$-$^{32}$P]ATP and ATPase assay, COS-1 cells were transfected by electroporation as previously described using 20 µg of the appropriate expression vectors (Moilanen et al., 1998b). Luciferase (LUC) and β-galactosidase activity measurements were carried out as described (Palvimo et al., 1996).

RNA Blotting, Immunocytochemistry and Immunoblotting

Poly(A)-containing RNA was isolated from rat tissues, resolved by agarose gel electrophoresis under denaturing conditions and transferred to Hybond membrane (Amersham Pharmacia Biotech) as previously described (Moilanen et al., 1998b). In addition to rat RNA samples, a mouse embryo RNA blot (CLONTECH) was hybridized with a $^{32}$P-labeled ARIP4 cDNA fragment corresponding to the ARID (amino acids 91–230). Final washes were carried out at high stringency [0.1×SSC (1×SSC is 0.15 M NaCl, 0.015 M sodium citrate) and 0.1% SDS, 52° C.], and the membranes subjected to autoradiography at −70° C.

ARIP4 antigen in transfected cells was detected by immunocytochemistry as previously described (Moilanen et al., 1998b). COS-1 cells seeded on cover slips were transfected using the FuGene reagent with 1 μg of pFLAG-ARIP4. Cells were fixed in 4% paraformaldehyde and permeabilized with Triton X-100. Ectopically expressed ARIP4 was detected either by anti-FLAG M2 monoclonal antiserum (1:50 dilution) or with anti-ARIP4 polyclonal rabbit antiserum (K7991, 1:1,000 dilution) and fluorescein isothiocyanate (FITC)-conjugated goat anti-mouse or anti-rabbit secondary antibody (1:200 dilution; Jackson ImmunoResearch Laboratories), respectively. Immunoblotting was conducted as previously described (Poukka et al., 1998) except that ARIP4 was detected with anti-ARIP4 antiserum (K7991, 1:2,000 dilution) and immunocomplexes were visualized with horseradish peroxidase-conjugated goat anti-(rabbit immunoglobulin G) antibody and the ECL detection reagents (Amersham Pharmacia Biotech.)

Protein-Protein Interaction in vitro

Affinity chromatography was carried out with bacterially expressed GST-AR ZFR or GST alone bound to glutathione-Sepharose (Moilanen et al., 1998b; Poukka et al., 1999). Translation in vitro was performed using the TNT coupled reticulocyte lysate system from Promega. Ten μl of [$^{35}$S] methionine-labeled translation product were mixed with GST or GST-AR ZFR in a buffer containing 50 mM Tris-HCl (pH 7.8), 50 mM KCl, 0.5 mM EDTA, 5 mM MgCl$_2$, 0.05 mM ZnCl$_2$, 10% glycerol, 0.4% Nonidet P-40, 0.1% Triton X-100, 0.5 mM PMSF, 6 μg/ml of aprotinin, and 5 μg/ml pepstatin in a total volume of 500 μl at 4° C. overnight. The beads were washed four times with 1 ml of binding buffer and bound proteins were resolved by SDS-PAGE and visualized by fluorography.

Immunoprecipitation and ATP-binding Assay

COS-1 cells electroporated with 10 μg of expression vectors encoding FLAG-tagged ARIP4, ARIP4K310A, ARIP4DE462AA and AR were lysed in buffer containing 20 mM Tris-HCl (pH 7.8), 140 mM NaCl, 1 mM EDTA, 0.1% Triton X-100, 0.5% Nonidet P-40, 1 mM dithiothreitol, 0.5 mM phenylmethylsulfonyl fluoride (PMSF), and 10 μg/ml of aprotinin. The cell lysates were clarified by centrifugation for 30 min at 16,000×g at 4° C. and adsorbed onto 50 μl of anti-FLAG M2 affinity matrix (Eastman Kodak). After immunoadsorption, the matrix was washed with 4 ml of lysis buffer followed by 4 ml of binding buffer containing 20 mM HEPES (pH 7.5), 100 mM KCl, 5 mM MgCl$_2$, 1 μM ZnCl$_2$, 0.1% Tween-20, 0.5 mM PMSF, and 10 μg/ml of aprotinin. The samples were kept as a 75% slurry. Ten μl of antibody-immobilized proteins were incubated with 4 μCi of 8-azido-[γ-$^{32}$P]ATP for 15 min at 22° C. in 20 μl of binding buffer in the absence or presence of 5 mM ATP. The reaction mixtures were irradiated at 3 cm from 254-nm light bulbs of UV Stratalinker 2400 (Stratagene), using the auto cross-link mode (120,000 μJ for 50 s). Cross-linked proteins were resolved by SDS-PAGE and visualized by autoradiography.

ATPase Assay

FLAG-tagged ARIP4, ARIP4K310A, ARIP4DE462AA and AR were expressed in COS-1 cells and immunopurified as for the ATPase assay except that proteins were eluted from the affinity matrix with buffer A (20 mM Tris-HCl, pH 7.5, 2 mM MgCl$_2$, 2 mM dithiothreitol, 5 mM KCl, and 150 mM NaCl) containing 0.2 mg/ml of the FLAG peptide. The assay mixture (15 μl) contained 11 μl of buffer B [buffer A supplemented with 100 μM ATP, 0.5 μCi of [γ-$^{32}$P]ATP (3000 Ci/mmol), 3 μl of immunopurified protein sample [or 100 fmol of nsP2 protein (Rikkonen et al., 1994) as the positive control], and 1 μl of ds-DNA (pGL3-Basic vector, Promega, 1 mg/ml) or water. After an 1-hr incubation at 37° C., 0.5 μl of the reaction mixture was spotted onto a poly(ethyleneimine)-cellulose thin-layer plate that was developed in 1 M LiCl and 1 M formic acid to resolve $^{32}$P$_i$, from [$^{32}$P]ATP. The plates were subjected to autoradiography and scanned on a phosphoimager to quantify the amount of $^{32}$P$_i$ released.

Results

Cloning of a New ATPase/Helicase-like Protein

Potential interaction partners for the zinc finger region (ZFR) of AR were identified by the use of the yeast two-hybrid screening technique with the hAR ZFR, including 20 amino acids of the hinge region, as the bait (AR ZFR, AR amino acids 544–644). AR ZFR was fused to LexA (LexA-AR ZFR), and the plasmid encoding the fusion construct employed to screen a size-selected 10.5-day-old mouse embryo cDNA library as previously described (Moilanen et al., 1998b). This screen yielded ~30 positive clones, which corresponded to six unique cDNA sequences that were all represented multiple times among the positive isolates. Three of the encoded proteins have already been characterized (Moilanen et al., 1998a; 1998b; 1999). To isolate a full-length cDNA encoding the fourth protein, mouse E11.5 λgt11 cDNA library was screened with two probes. The first sequence (FIG. 1A, probe 1) representing the AR interaction domain (ARID) identified a 4.0-kb-long cDNA fragment containing a long open reading frame preceded by an in-frame stop codon. The second probe corresponded to the 3'-end of the 4.0-kb cDNA (FIG. 1A, probe 2), and rescreening of the λgt11 cDNA library with this sequence led to the isolation of an additional clone that covered the complete 3'-end of the protein-coding sequence as well as part of the 3'-untranslated region. The deduced sequence predicts a 1466-amino-acid-long protein that is termed ARIP4 (for androgen receptor-interacting protein 4) (FIG. 1B).

ARIP4 has a calculated molecular mass of 160 kDa, a net charge of −18.2 at pH 7.5 and an isoelectric point of 6.4. When ectopically expressed in COS-1 cells, the immunoreactive protein migrates on SDS-PAGE with an apparent molecular mass of 180 kDa (FIG. 1C). Expression of pFLAG-ARIP4 in COS-1 cells results in nuclear localization of ARIP4 antigen, as visualized by immunocytochemical analyses using either anti-FLAG or anti-ARIP4 antibodies (FIG. 1D). It is of note that ARIP4 is not evenly distributed in recipient cell nuclei but the immunoreactivity exhibits a speckled pattern. ARIP4 sequence includes at least three putative bipartite nuclear localization signals (amino acids 98–114; 412–428; and 1254–1271). The amino-terminal region (amino acids 21–260), including the AR interaction domain (ARID, amino acids 91–230), is very rich in negatively charged amino acids (FIG. 1B), a feature typical of many proteins involved in transcriptional regulation.

Figure 2:
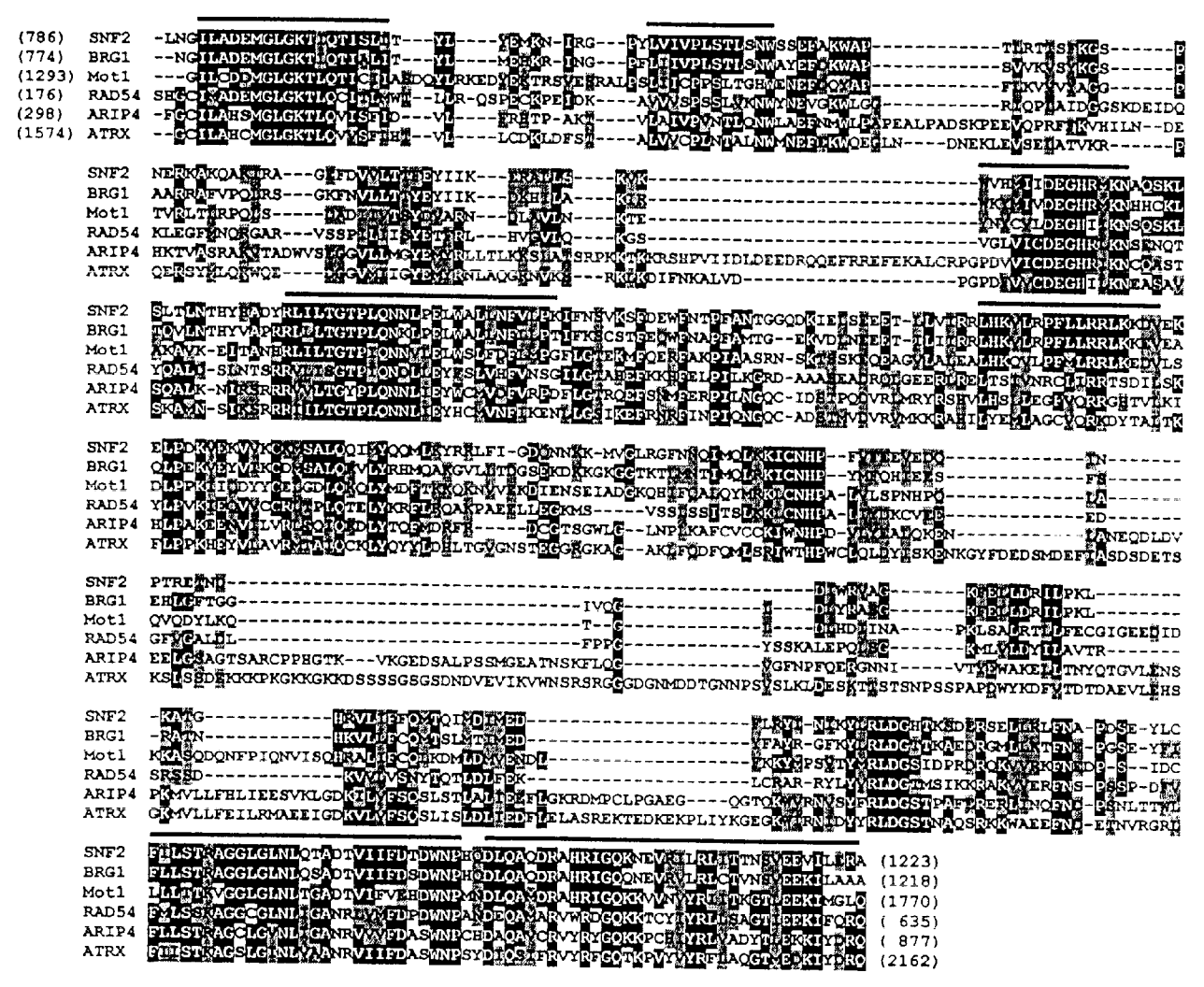

ARIP4 contains a region with a strong amino acid sequence homology to proteins in the SNF2-like family of ATPases/putative helicases, and all the seven helicase motifs shared by the family members are included in the ARIP4 sequence (FIGS. 1B and 2), with the ATRX protein (Picketts et al., 1996) showing the highest homology in the helicase domains. The sequence similarity was restricted to the Snf2 domain, and no protein homologous to ARIP4 outside the Snf2 domain has thus far been isolated and characterized. However, a predicted protein sequence (KIAA0809 protein) of an unidentified human gene that exhibits >95% amino acid sequence identity with ARIP4 in their overlap, covering amino acids 225–1466 of ARIP4, has been deposited into GenBank (accession number BAA34529). Northern blot analysis of RNA samples from several rat tissues and from mouse embryo of days 7 to 15 revealed that ARIP4 is encoded by an ~9.0-kb mRNA that is expressed at a relatively low level (FIG. 3). In addition, there are multiple ARIP4 mRNA species of smaller size, especially in the testis and prostate.

ARIP4 Binds ATP and Possesses Intrinsic ATPase Activity

Several SNF2-like family members exhibit ATP-hydrolyzing activity (Laurent et al., 1993; Auble et al., 1994). To examine whether ARIP4 is capable of binding ATP, FLAG-tagged ARIP4 and two ARIP4 forms with mutations in the putative catalytic center (FLAG-ARIP4K310A and FLAG-ARIP4DE462AA) were immunopurified, and the isolated proteins were incubated with a photo-reactive ATP analogue, 8-azido-[γ-$^{32}$P]ATP. UV irradiation of ARIP4 with 8-azido-[γ-$^{32}$P]ATP resulted in cross-linking of [$^{32}$P]ATP to the protein (FIG. 4A, lane 3). ARIP4K310A and ARIP4DE462AA were also affinity-labeled with 8-azido-[γ-$^{32}$P]ATP, but somewhat less efficiently than the wild-type protein (FIG. 4A, lanes 5 and 7). Immunopurified AR (a control protein) was not labeled by 8-azido-[γ-$^{32}$P]ATP in a specific fashion under the same conditions (FIG. 4A, lane 1). Affinity-labeling of ARIP4 proteins with 8-azido-[γ-$^{32}$P]ATP was abolished by a 1000-fold molar excess of nonradioactive ATP, attesting to the specificity of the cross-linking reaction.

To measure ATPase activity of ARIP4, the FLAG-tagged wild-type protein together with the mutants ARIP4K310A and ARIP4DE462AA were purified by immunoadsorption. Semliki forest virus nonstructural protein 2 (nsP2, Rikkonen et al., 1994) served as the positive and FLAG-tagged AR as the negative control in the assay. ATPase activity of ARIP4 was strictly dependent on the presence of double-stranded DNA in the assay mixture, and the two ARIP mutants along with AR were completely devoid of ATPase activity (FIG. 4B). The amounts of FLAG-tagged ARIP4 proteins were not significantly different in the experiments presented in FIG. 4 (data not shown).

ARIP4 Interacts with AR in vivo and in vitro

The interaction between AR and ARIP4 was assessed in yeast and in mammalian cells. In L40 yeast cells, different regions of AR fused to LexA, including the original bait construct (LexA-AR ZFR, AR amino acids 554–644), were co-expressed with the Herpex simplex VP16 activation domain (VP16 AD) alone or with VP16 AD fused to amino acids 86–227 of ARIP4 (VP16-ARIP4 ID). Coexpression of VP16-ARIP4 ID and LexA-AR ZFR increased the reporter gene activity by ~100-fold over that with Lex-AR ZFR and VP16 AD alone (FIG. 5A). VP16-ARIP4 ID also interacted very strongly with full-length AR fused to LexA (LexA-AR); this interaction was strictly dependent on the presence of androgen (FIG. 5A). Deletion of the 20 hinge region residues from the original bait construct (LexA ZFR-s, AR amino acids 554–623) weakened the interaction with VP16-ARIP4 ID markedly, suggesting that the N-terminal hinge residues either participate in the interaction with ARIP4 or are essential for the ZFR to fold properly. A LexA fusion protein including the hinge residues and the AR ligand-binding domain (LexA-HLBD, AR amino acids 624–919) exhibited rather weak interaction with VP16-ARIP4 ID in the presence of androgen; it was ~4-fold over that with VP16 AD alone (FIG. 5A). When ZFRs of estrogen and progesterone receptors were fused to LexA, the fusion proteins possessed measurable interaction with VP16-ARIP4 ID, which was 20–30% of that with AR ZFR (data not shown).

In mammalian cells, ARIP4 ID fused to VP16 AD interacts with full-length AR fused in-frame to Gal4 DBD, as judged by the activation of a reporter gene driven by Gal4 DNA-binding motifs (FIG. 5B). There was some interaction with ARIP4 ID and Gal4-AR in the absence of androgen (~5-fold increase), but the interaction was much stronger in the presence than absence of 100 mM testosterone in culture medium (>10-fold increase). The small nuclear RING finger protein (SNURF) and human ornithine decarboxylase (ODC) fused to VP16 AD served in these experiments as the positive and the negative control, respectively (FIG. 5B). SNURF is an AR coregulator (Moilanen et al., 1998b), and it interacts with AR ZFR both in vitro and in vivo (Moilanen et al., 1998b). By contrast, ODC is a cytoplasmic protein that is not anticipated to interact with nuclear receptors. The interaction of ARIP4 ID with Gal4-AR was stronger than that of SNURF with the receptor, whereas ODC failed to recognize Gal4-AR (FIG. 5B).

To assess whether ARIP4 interacts directly with AR under cell-free conditions, GST pull-down experiments were performed using ARIP4 labeled with [$^{35}$S]methionine by translation in vitro and AR ZFR adsorbed to glutathione-Sepharose beads (GST-ZFR). After the incubation of $^{35}$S-labeled ARIP4 with the GST-ZFR matrix, the beads were washed and bound proteins were resolved by SDS-PAGE. ARIP4 interacted specifically with GST-ZFR (FIG. 6, lane 3), and no ARIP4 adhered to control beads (lane 2). [$^{35}$S] Methionine-labeled luciferase (LUC) served as a negative control in these studies, and it did not exhibit any binding to GST-ZFR (FIG. 6, lane 5).

Effect of ARIP4 on AR-Dependent Transcription

Other proteins in the SNF2-like family have previously been demonstrated to cooperate with the activity of some nuclear receptors (Yoshinaga et al., 1992; Muchardt and Yaniv, 1993; Chiba et al., 1994; Ichinose et al., 1997). To assess the influence of ARIP4 on the transactivation ability of AR, transient co-transfections were performed in COS-1 cells using reporter constructs driven by different promoters. In addition to wild-type ARIP4, several mutated ARIP4 forms were transfected with AR. Coexpression of ARIP4 with AR increased the transcriptional activity of AR on a minimal promoter (ARE$_4$-tk, FIG. 7A) ~3-fold, whereas an ARIP4 form devoid of the N-terminus, including the AR interaction domain (ARID; ARIP4 1–280), did not influence AR function. Truncation of ARIP4 at the C-terminus (ARIP4 1315–1466) generated a protein that was significantly less active than wild-type ARIP4, suggesting that there are functionally important interaction surfaces in the C-terminal region of ARIP4. Interestingly, the ARIP4 mutants devoid of ATPase activity (ARIP4K310A and ARIP4DE462AA) were unable to activate AR function; rather, when co-expressed with AR, these two ARIP4 forms behaved as trans-dominant negative regulators of AR function (FIG. 7A). ARIP4 cDNA sequence expressed in reverse orientation did not modulate AR function significantly. Similar to ARE$_4$-tk, wild-type ARIP4 activated AR function and the ATPase-deficient mutants behaved as trans-dominant negative regulators of AR on ARE$_2$-TATA, another minimal promoter (data not shown).

In contrast to AR-dependent minimal promoters, the influence of ARIP4 in transient transfection assays on the regulation of the natural probasin promoter (−285/+32) by AR were less dramatic and always inhibitory (FIG. 7B). Thus, wild-type ARIP4 and the ATPase-deficient mutants attenuated AR activity to 50–60% of that of AR alone. Deletion of the ARID (ARIP4Δ1–280) or residues 1315–1466 (ARIP4 1315–1466) relieved the repressive action of wild-type ARIP4 (FIG. 7B). Immunoblot analyses indicated that wild-type and mutant ARIP4 proteins were expressed to comparable levels under the conditions used (FIG. 1C, and data not shown).

Discussion

Like other steroid receptors, AR contains two transactivation functions; AF-1 in the N-terminal region and AF-2 in the hormone-binding domain (Quigley et al., 1995). In contrast to other members of this nuclear receptor subfamily, the activity of AR AF-1 is much stronger to that of AF-2 (Moilanen et al., 1997) which can be, however, activated through interaction with multiple coregulatory proteins (Ikonen et al., 1997; Torchia et al., 1998; McKenna et al., 1999; Freedman, 1999). The zinc finger region of AR (AR ZFR) also presents an interaction interface for proteins, including those needed in trans-repression of AP1- and NF-κB-activated genes, in part through a mechanism involving CREB-binding protein, CBP (Kallio et al., 1995; Palvimo et al., 1999; Aarnisalo et al., 1998). We have previously characterized three new proteins interacting with AR ZFR and shown that each one behaves as an AR coregulator (Moilanen et al., 1998a; 1998b; 1999). The fourth AR ZFR-interacting protein described herein, ARIP4, is a novel member of the SNF2-like family. ARIP4 binds ATP and possesses DNA-dependent ATPase activity, similar to several other proteins of this family (Kingston and Narlikar, 1999). The interaction interface for AR ZFR resides in a non-conserved region located N-terminal to the ATPase domain of ARIP4. Thus, ATPase activity of ARIP4 may be recruited to AR-regulated chromatin regions through its interaction with the receptor.

The proteins of the SNF2-like family comprise members that play multiple roles in the regulation of protein-DNA interactions, such as those involved in transcription, replication and repair, and contain a large conserved Snf2 domain that confers ATPase activity on the proteins (Pazin and Kadonaga, 1997; Kingston and Narlikar, 1999). The Snf2 domain is surrounded by non-conserved regions that are thought to determine the nuclear context in which the ATPase activity is needed (Eisen et al., 1995). The initial connection of SWI/SNF proteins to steroid receptor-dependent transcription was the demonstration that GR activity, expressed in yeast, requires these complexes and that reporter activation brought about by GR or ER is lost in yeast strains deficient for SWI1, SWI2, and SWI3 proteins (Yoshinaga et al., 1992). Subsequent studies showed that ectopically expressed mammalian SWI2/SNF2 homologs, hbrm and BGR1, cooperate with GR or ER in trans-activation of reporter genes (Muchardt and Yaniv, 1993; Chiba et al., 1994; Fryer and Archer, 1998), that GR increases the SWI/SNF nucleosome remodeling activity when bound to a nucleosomal glucocorticoid response element (Östlund Farrangs et al., 1997), and that glucocorticoids promote hormone-induced association of GR to the BRG1 complex in vivo (Fryer and Archer, 1998).

Diverse regions of steroid receptors are implicated in the interaction with SNF2-like proteins. An intact DNA-binding domain (zinc finger region) of GR was shown to be needed for the receptor's cooperation with SWI2/SNF2 proteins and their mammalian homologs (Yoshinaga et al., 1992; Muchardt and Yaniv, 1993). By contrast, the ligand-binding domain of ER comprising the AF-2 function interacted in a yeast two-hybrid assay with the N-terminal region preceding the ATPase domain of hbrm or BRG1 (Ichinose et al., 1997). Another ATPase, p68 RNA helicase, was recently shown to be a coactivator of ERα function and to interact with the N terminus containing AF-1 of this receptor (Endoh et al., 1999). Our present data link AR function to a novel member of the SNF2-like family, ARIP4, the N-terminal region of which interacts with AR ZFR. Deletion of the AR interaction interface (ARID) abolished the activity of ARIP4 on AR function. Comparison of this ARID to those in three other proteins interacting with AR ZFR (Moilanen et al., 1998a; 1998b; 1999) fails to define a consensus sequence, although each surface contains a Ser-rich cluster of charged amino acids (Asp, Arg, Glu, and Lys) flanked by non-polar residues (Ile, Leu, and Val).

The ATPase activity of ARIP4 was mandatory for its ability to activate AR function, a situation similar to that with GR activation by hbrm (Muchardt and Yaniv, 1993) and to the function of many other, but not all, SNF2-like family members (Khavari et al., 1993; Laurent et al., 1993; Auble et al., 1994; Kingston and Narlikar, 1999; Tyler and Kadonaga, 1999). Like the ATPase-deficient ARIP4 mutants ARIP4K310A and ARIP4DE462AA in mammalian cells, MOT1 mutants devoid of ATPase activity behaved as trans-dominant negative alleles in yeast (Auble et al., 1994). Mechanisms for this feature are currently unknown, but perhaps ARIP4 without catalytic ATPase activity locks other partners interacting with endogenous ARIP4, or a related protein, in a nonfunctional complex. Determination of the nature of nuclear proteins complexed with ARIP4 in vivo would help to resolve this issue. The C-terminal region of ARIP4 does not exhibit sequence homology with any SNF2-like family members or contain recognizable functional domains, such a bromodomain or a SANT domain (Kingston and Narlikar, 1999). However, deletion of the ~150 C-terminal residues attenuated ARIP4 activity, implying that ATPase activity is mandatory but not sufficient for its ability to modulate AR function.

ATP-driven chromatin remodeling factors facilitate not only transcriptional activation, but also repression (Kingston and Narlikar, 1999; Tyler and Kadonaga, 1999). For example, genome-wide expression analysis in yeast revealed that, of the genes dependent on the SWI/SNF complex (~6% of all yeast genes), a greater number was negatively rather than positively regulated by SWI/SNF (Holstege et al., 1998). Likewise, the c-fos promoter is repressed by BRG1 the mechanism of which requires the presence of the Rb protein (Murphy et al., 1999). Transcription activation by SWI/SNF is attributed to interaction of the SWI/SNF complex with acidic activators, whereas recruitment of histone deacetylase activity by chromatin remodeling complexes is involved in transcriptional repression (Neely et al., 1999; Tong et al., 1998; Tyler and Kadonaga, 1999). In view of this, it was not totally unexpected that AR-dependent minimal promoters, $ARE_4$-tk and $ARE_2$-TATA, were regulated by ectopic ARIP4 expression in a fashion different from that of probasin and MMTV promoters (FIG. 7 and unpublished results). Since the latter two promoters contain a complex pattern of DNA motifs besides the androgen response elements, ARIP4 may attenuate the interaction of relevant trans-acting factors with these cis-elements. We cannot exclude the possibility that, similar to another SNF2-like family member, MOT1 (Auble et al., 1997), ARIP4 influences DNA binding of the receptor itself in a promoter-specific fashion.

Targeting of Snf2 domain-containing chromatin remodeling complexes in vivo to specific DNA sequences can be achieved (i) by recruitment of sequence-specific transcription factors, (ii) through interaction with the RNA polymerase holoenzyme, or (iii) by intrinsic DNA-binding ability (Björklund et al., 1999; Kingston and Narlikar, 1999; Lemon and Freedman, 1999). It is tempting to suggest that targeting of ARIP4-containing complexes to AR-dependent genes occurs through AR, a sequence-specific transcription factor. Nevertheless, it remains to be established whether ARIP4 possesses intrinsic DNA-binding activity that would, in turn, be able to target AR to requisite regulatory regions. In any event, ARIP4 is the first SNF2-like protein shown to interact with the AR, and it is also a novel member of this protein family. Better understanding of its function—or that of other SNF2-like proteins—in steroid receptor signaling requires improved knowledge of the proteins that ARIP4 is complexed in vivo and the ways by which ARIP4 facilitates nucleosome assembly and mobilization during transcriptional activation and repression. It would be of particular interest to determine whether ARIP4 forms complexes in vivo with other AR ZFR-interacting proteins; the small nuclear RING finger protein SNURF (Moilanen et al., 1998b); the novel nuclear Ser/Thr kinase ANPK (Moilanen et al., 1998a); and ARIP3, a member of the PIAS family (Moilanen et al., 1999). And finally, it is an intriguing possibility that ARIP4 would be covalently modified in reactions catalyzed by ANPK or Ubc9, another protein interacting with the AR ZFR (Poukka et al., 1999).

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

References

Aarnisalo, P., Palvimo, J. J., and Jänne, O. A. (1998). CREB-binding protein in androgen receptor-mediated signalling. Proc. Natl. Acad. Sci. USA 95, 2122–2127.

Asubel, F. M., Brent, R., Kingston, R. E., Moore, D. D., Seidman, J. G., Smith, J. A., and Struhl, K. (1997). Current protocols in molecular biology. John Wiley & Sons, New York, N.Y.

Auble, D. T., Hansen, K. E., Mueller, C. G. F., Lane, W. S., Thorner, J., and Hahn, S. (1994). Mot1, a global repressor of RNA polymerase II transcription, inhibits TBP binding to DNA by an ATP-dependent mechanism. Genes Dev. 8, 1920–1934.

Auble, D. T., Wang, D., Post, K. W., and Hahn, S. (1997). Molecular analysis of the SNF2/SWI2 protein family member MOT1, an ATP-driven enzyme that dissociates TATA-binding protein from DNA. Mol. Cell. Biol. 17, 4842–4851.

Beato, M., Herrlich, P., and Schütz, G. (1995). Steroid hormone receptors: many actors in search of a plot. Cell 83, 835–839.

Björklund, S., Almouzni, G., Davidson, I., Nightingale, K. P., and Weiss, K. (1999). Global transcription regulators of eukaryotes. Cell 96, 759–767.

Blanco, J. C. G., Wang, I.-M., Tsai, S. Y., Tsai, M.-J., O'Malley, B. W., Jurutka, P. W., Haussler, M. R., and Ozato, K. (1995). Transcription factor TFIIB and the vitamin D receptor cooperatively activate ligand-dependent transcription. Proc. Natl. Acad. Sci. USA 92, 1535–1539.

Chiba, H., Muramatsu, M., Nomoto, A., and Kato, H. (1994). Two human homologues of Saccharomyces cerevisiae SWI2/SNF2 and Drosophila brahma are transcriptional coactivators cooperating with the estrogen receptor and the retinoic acid receptor. Nucleic Acids Res. 22, 1815–1820.

Cote, J., Quinn, J., Workman, J. L., and Peterson, C. L. (1994). Stimulation of GAL4 derivative binding to nucleosomal DNA by the yeast SWI/SNF complex. Science 265, 53–60.

Davis, J. L., Kunisawa, R., and Thorner, J. (1992). A presumptive helicase (MOT1 gene product) affects gene expression and is required for viability in yeast Saccharomyces cerevisiae. Mol. Cell. Biol. 12, 1879–1892.

Eisen, J. A., Sweder, K. S., and Hanawalt, P. C. (1995). Evolution of the SNF2 family of proteins: subfamilies with distinct sequences and functions. Nucleic Acids Res. 23, 2715–2723.

Emery, H. S., Schild, D., Kellogg, D. E., and Mortimer, R. K. (1991). Sequence of RAD54, a Saccharomyces cerevisiae gene involved in recombination and repair. Gene 104, 103–106.

Endoh, H., Maruyama, K., Masuhiro, Y., Kobayashi, Y., Goto, M., Tai, H., Yanagisawa, J., Metzger, D., Hashimoto, S., and Kato, S. (1999). Purification and identification of p68 RNA helicase acting as a transcriptional coactivator specific for the activation function 1 of human estrogen receptor α. Mol. Cell. Biol. 19, 5363–5372.

Freedman, L. P. (1999). Increasing the complexity of coactivation in nuclear receptor signaling. Cell 97, 5–8.

Fryer, C. J., and Archer, T. J. (1998). Chromatin remodelling by the glucocorticoid receptor requires the BRG1 complex. Nature 393, 88–91.

Hadzic, E., Desai-Yajnik, V., Helmer, E., Guo, S., Wu, S., Koudinova, N., Casanova, J., Raaka, B. M., and Samuels, H. H. (1995). A 10-amino-acid sequence in the N-terminal A/B domain of thyroid hormone receptor alpha is essential for transcriptional activation and interaction with the general transcription factor TFIIB. Mol. Cell. Biol. 15, 4507–4517.

Hirschhorn, J. N., Brown, S. A., Clark, C. D., and Winston, F. (1992). Evidence that SNF2/SWI2 and SNF5 activate transcription in yeast by altering chromatin structure. Genes Dev. 6, 2288–2298.

Holstege, F. C. P., Jennings, E. G., Wyrick, J. J., Ihn Lee, T., Hengartner, C. J., Green, M. R., Golub, T. R., Lander, E. C., and Young, R. A. (1998). Dissecting the regulatory circuitry of a eukaryotic genome. Cell 95, 717–728.

Ichinose, H., Garnier, J.-M., Chambon, P., and Losson, R. (1997). Ligand-dependent interaction between the estrogen receptor and the human homologues of SWI2/SNF2. Gene 188, 95–100.

Ikonen, T., Palvimo, J. J., and Jänne, O. A. (1997). Interaction between the amino- and carboxyl-terminal regions of the rat androgen receptor modulates transcriptional activity and is influenced by nuclear receptor coactivators. J. Biol. Chem. 272, 29821–29828.

Ing, N. H., Beekman, J. M., Tsai, S. Y., Tsai, M-J., and O'Malley, B. W. (1992). Members of the steroid hormone receptor superfamily interact with TFIIB (S300-II). J. Biol. Chem. 267, 17617–17623.

Ito, T., Levenstein, M. E., Fyodorov, D. V., Kutach, A. K., Kobayashi, R., and Kadonaga, J. T. (1999). ACF consists of two subunits, acf1 and ISWI, that function cooperatively in the ATP-dependent catalysis of chromatin assembly. Genes Dev. 13, 1529–1539.

Kallio, P. J., Poukka, H., Moilanen, A., Jänne, O. A., and Palvimo, J. J. (1995). Androgen receptor mediated transcriptional regulation in the absence of direct interaction with a specific DNA element. Mol. Endocrinol. 9, 1017–1028.

Khavari, P. A., Peterson, C. L., Tamkun, J. W., Mendel, D. B., and Crabtree, G. R. (1993). BRG1 contains a conserved domain of the SWI2/SNF2 family necessary for normal mitotic growth and transcription. Nature 366, 170–174.

Kingston, R. E., Bunker, C. A., and Imbalzano, A. N. (1996). Repression and activation by multiprotein complexes that alter chromatin structure. Genes Dev. 10, 905–920.

Kingston, R. E., and Narlikar, G. J. (1999). ATP-dependent remodeling and acetylation as regulators of chromatin fluidity. Genes Dev. 13, 2339–2352.

Kwon, H., Imbalzano, A. N, Khavari, P. A., Kingston, R. E., and Green, M. R. (1994). Nucleosome disruption and enhancement of activator binding by a human SWI/SNF complex. Nature 370, 477–481.

Laurent, B. C., and Carlson, M. (1992). Yeast SNF2/SWI2, SNF5, and SNF6 proteins function coordinately with the gene-specific transcriptional activators GAL4 and Biocoid. Genes Dev. 6, 1707–1715.

Laurent, B. C., Treich, I., and Carlson, M. (1993). The yeast SNF2/SWI2 protein has DNA-stimulated ATPase activity required for transcriptional activation. Genes Dev. 7, 583–591.

Lemon, B. D., and Freedman, L. P. (1999). Nuclear receptor cofactors as chromatin remodelers. Curr. Opin. Genet. Devel. 9, 499–504.

LeRoy, G., Orphanides, G., Lane, W. S., and Reinberg, D. (1998). Requirement of RSF and FACT for transcription of chromatin templates in vitro. Science 282, 1900–1904.

McEwan, I. J., and Gustafsson, J.-Å. (1997). Interaction of the human androgen receptor transactivation function with the general transcription factor TFIIF. Proc. Natl. Acad. Sci. USA 94, 8485–8490.

McKenna, N. J., Lanz, R. B., and O'Malley, B. W. (1999). Nuclear receptor coregulators: cellular and molecular biology. Endocr. Rev. 20, 321—344.

Mizuguchi, G., Tsukiyama, T., Wisniewski, J., and Wu, C. (1997). Role of nucleosome remodeling factor NURF in transcriptional activation of chromatin. Mol. Cell 1, 141–150.

Moilanen, A., Rouleau, N., Ikonen, T., Palvimo, J. J., and Jänne, O. A. (1997). The presence of a transcription activation function in the hormone-binding domain of androgen receptor is revealed by studies in yeast cells. FEBS Lett. 412, 355–358.

Moilanen, A-M., Karvonen, U., Poukka, H., Jänne, O. A., and Palvimo, J. J. (1998a). Activation of androgen receptor function by a novel nuclear protein kinase. Mol. Biol. Cell 9, 2527–2543.

Moilanen, A-M., Karvonen, U., Poukka, H., Yan, W., Toppari, J., Jänne, O. A., and Palvimo, J. J. (1999). A testis-specific coregulator of androgen receptor that belongs to a novel family of nuclear proteins. J. Biol. Chem. 274, 3700–3704.

Moilanen, A-M., Poukka, H., Karvonen, U., Hakli, M., Jänne, O. A., and Palvimo, J. J. (1998b). Identification of a novel RING finger protein as a coregulator in steroid receptor-mediated gene transcription. Mol. Cell. Biol. 18, 5128–5139.

Muchardt, C., and Yaniv, M. (1993). A human homologue of Saccharomyces cerevisiae SNF2/SWI2 and Drosophila brm genes potentiates transcriptional activation by the glucocorticoid receptor. EMBO J. 12, 4279–4290.

Murphy, D. J., Hardy, S., and Engel, D. A. (1999). Human SWI-SNF component BRG1 represses transcription of the c-fos gene. Mol. Cell. Biol. 19, 2724–2733.

Neely K. E., Hassan, A. H., Wallberg, A. E., Steger, D. J., Cairns B. R., Wright, A. P. H., and Workman, J. L. (1999) Activation domain-mediated targeting of the SWI/SNF complex to promoter stimulates transcription from nucleosome arrays. Mol. Cell 4, 649–655.

Östlund Farrangs, A-K., Blomquist, P., Kwon, H., and Wrange, Ö. (1997). Glucocorticoid receptor-glucocorticoid response element binding stimulates nucleosome disruption by the SWI/SNF complex. Mol. Cell. Biol. 17, 895–905.

Palvimo, J. J., Reinikainen, P., Ikonen, T., Kallio, P. J., Moilanen, A., and Jänne, O. A. (1996). Mutual transcriptional interference between RelA and androgen receptor. J. Biol. Chem. 271, 24151–24156.

Pazin, M. J., and Kadonaga, J. T. (1997). SWI2/SNF2 and related proteins: ATP-driven motors that disrupt protein-DNA interactions? Cell 88, 737–740.

Perlmann, T., and Evans, R. M. (1997). Nuclear receptors in Sicily: All in the famiglia. Cell 90, 391–397.

Picketts, D. J., Higgs, D. R., Bachoo, S., Blake, D. J., Quarrell, O. W. J., and Gibbons, R. J. (1996). ATRX encodes a novel member of the SNF2 family of proteins: mutations point to a common mechanism underlying the ATR-X syndrome. Hum. Mol. Genet. 5, 1899–1907.

Poukka, H., Aarnisalo, P., Karvonen, U., Palvimo, J. J., and Jänne, O. A. (1999). Ubc9 interacts with the androgen receptor and activates receptor-dependent transcription. J. Biol. Chem. 274, 19441–19446.

Quigley, C. A., de Bellis, A., Marschke, K. B., El-Awady, M. K., Wilson, E. M., and French, F. S. (1995). Androgen receptor defects: historical, clinical, and molecular perspectives. Endocr. Rev. 16, 271–321.

Richmond, E., and Peterson, C. L. (1996). Functional analysis of the DNA-stimulated ATPase domain of yeast SWI2/SNF2. Nucleic Acid Res. 24, 3685–3692.

Rikkonen, M., Peränen, J., and Kääriäinen, L. (1994). ATPase and GTPase activities associated with Semliki forest virus nonstructural protein nsP2. J. Virol. 68, 5804–5810.

Tong, J. K., Hassig, C. A., Schnitzler, G. R., Kingston, R. E., and Schreiber, S. L. (1998). Chromatin deacetylation by an ATP-dependent nucleosome remodelling complex. Nature 395, 917–921.

Torchia, J., Glass, C., and Rosenfeld, M. G. (1998). Co-activators and co-repressors in the integration of transcriptional responses. Curr. Opin. Cell. Biol. 10, 373–383.

Tsuchiya, E., Hosotani, T., and Miyakawa, T. (1998). A mutation in NPS1/STH1, an essential gene encoding a component of a novel chromatin-remodeling complex RSC, alters the chromatin structure of Saccharomyces cerevisiae centromeres. Nucleic Acids Res. 26, 3286–3292.

Tyler, J. K., and Kadonaga, J. T. (1999). The "dark side" of chromatin remodeling: repressive effects on transcription. Cell 99, 443–446.

Varga-Weisz, P. D., Wilm, M., Bonte, E., Dumas, K., Mann, M., and Becker, P. B. (1997). Chromatin-remodelling factor CHRAC contains the ATPases ISWI and topoisomerase II. Nature 388, 598–602.

Xue, Y., Wong, J., Moreno, G. T., Young, M. K., Cote, J., and Wang, W. (1998). NURD, a novel complex with both ATP-dependent chromatin-remodeling and histone deacetylase activities. Mol. Cell 6, 851–861.

Yoshinaga, S. K., Peterson, C. L., Herskowitz, I., and Yamamoto, K. R. (1992). Roles of SWI1, SWI2, and SWI3 proteins for transcriptional enhancement by steroid receptors. Science 258, 1598–1604.

What is claimed is:

1. An isolated protein being able to bind to the androgen receptor and having ATPase activity, said protein comprising the amino acid sequence set forth in SEQ ID NO: 2.

2. An isolated protein consisting essentially of the amino acids 91 to 230 set forth in SEQ ID NO:2, wherein the isolated protein has ATPase activity.

3. An isolated protein consisting essentially of the regions I, Ia, II, III, IV, V and VI, wherein region I consists essentially of the amino acids 301–318 of SEQ ID NO:2, region Ia consists essentially of the amino acids 333–346 of SEQ ID NO:2, region II consists essentially of the amino acids 455–469 of SEQ ID NO:2, region III consists essentially of the amino acids 485–502 of SEQ ID NO:2, region IV consists essentially of the amino acids 737–754 of SEQ ID NO:2, region V consists essentially of the amino acids 809–838 of SEQ ID NO:2, region VI consists essentially of the amino acids 839–874 of SEQ ID NO:2 and the isolated protein has ATPase activity.

4. An isolated protein consisting essentially of the amino acids 301 to 874 set forth in SEQ ID NO:2, wherein the isolated protein has ATPase activity.

* * * * *

SEQUENCE LISTING

<160> NUMBER OF SEQ ID NOS: 7

<210> SEQ ID NO 1
<211> LENGTH: 5066
<212> TYPE: DNA
<213> ORGANISM: Mus musculus
<220> FEATURE:
<221> NAME/KEY: CDS
<222> LOCATION: (191)..(4588)

<400> SEQUENCE: 1

```
gcgccgcagg ctggctctgg ccgagggtcg gtcttctccg gctcccgccg ccgcagacac      60
cgtccaagag ggtgcggcag aacgcgaggt cctacggccc agcccggtcc ggtgcggccc     120
ggatccgtgg cacgggagga ccctactgtg gacatgagtc ggtaatgccc actgaggact     180
tctgggagcc atg tca gac gaa tcc gcc tca ggg agc gat cca gac ctg        229
           Met Ser Asp Glu Ser Ala Ser Gly Ser Asp Pro Asp Leu
             1               5                  10 gac ccg gac gtg gag ctg gag gat gag gaa gag gag gag gag gag gag        277
Asp Pro Asp Val Glu Leu Glu Asp Glu Glu Glu Glu Glu Glu Glu Glu
         15                  20                  25 gag gtg gca gtg gag gag cat gac agg gat gac gag gaa ggc ctg ctg        325
Glu Val Ala Val Glu Glu His Asp Arg Asp Asp Glu Glu Gly Leu Leu
 30                  35                  40                  45 gat gac aca tcc ctg gaa ggc atg tgt ggc act gag cat gcc cag ctg        373
Asp Asp Thr Ser Leu Glu Gly Met Cys Gly Thr Glu His Ala Gln Leu
                 50                  55                  60 ggg gaa gat ggg cag cgg ccg ccg cgg tgc act tca act acc tca tct        421
Gly Glu Asp Gly Gln Arg Pro Pro Arg Cys Thr Ser Thr Thr Ser Ser
             65                  70                  75 cag tct gag cct tca gag cag ctt agg cac caa ggc aag atc cta gca        469
Gln Ser Glu Pro Ser Glu Gln Leu Arg His Gln Gly Lys Ile Leu Ala
         80                  85                  90 tcc gag gac ccc aaa aag aag cga gct cag aag ccc tct cac atg aga        517
Ser Glu Asp Pro Lys Lys Lys Arg Ala Gln Lys Pro Ser His Met Arg
     95                 100                 105 aga aac ata cga aag cta ctc cgg gag gat cag ttg gag ccc gta acc        565
Arg Asn Ile Arg Lys Leu Leu Arg Glu Asp Gln Leu Glu Pro Val Thr
110                 115                 120                 125 aaa gca gca cag cag gaa gaa ttg gaa aga aga aag cgc ctg gag cag        613
Lys Ala Ala Gln Gln Glu Glu Leu Glu Arg Arg Lys Arg Leu Glu Gln
                130                 135                 140 cag agg aaa gaa tat gca gcc ccc att cct act gtc cct ttg gag ttc        661
Gln Arg Lys Glu Tyr Ala Ala Pro Ile Pro Thr Val Pro Leu Glu Phe
            145                 150                 155 cta cct gag gaa att gtc tta cga gct agt gat ggt ccc cag ctc cca        709
Leu Pro Glu Glu Ile Val Leu Arg Ala Ser Asp Gly Pro Gln Leu Pro
        160                 165                 170 cct cgg gtc tta gcc cag gaa gtc att tgt ttg gac agt agc agt ggc        757
Pro Arg Val Leu Ala Gln Glu Val Ile Cys Leu Asp Ser Ser Ser Gly
    175                 180                 185 agt gag gat gaa aag agt agt cga gac gag gta att gag ctg agt tct        805
Ser Glu Asp Glu Lys Ser Ser Arg Asp Glu Val Ile Glu Leu Ser Ser
190                 195                 200                 205 gga gag gag gat acg ctg cac atc gtg gac agc agt gag tct gtc agc        853
Gly Glu Glu Asp Thr Leu His Ile Val Asp Ser Ser Glu Ser Val Ser
                210                 215                 220 gag gag gac gag gaa gag gag aag ggt ggc acc cat gtg aat gac gcc        901
Glu Glu Asp Glu Glu Glu Glu Lys Gly Gly Thr His Val Asn Asp Ala
```

-continued

| | | |
|---|---|---|
| tta aac cag cat gat gct ctc ggg cgg gtc ctt gtc aac ctg aat cac<br>Leu Asn Gln His Asp Ala Leu Gly Arg Val Leu Val Asn Leu Asn His<br>                240                            245                            250 | 949 |
| cct cca gag gag gag aat gtc ttc ctg gcc ccc cag ttg gca cgg gct<br>Pro Pro Glu Glu Glu Asn Val Phe Leu Ala Pro Gln Leu Ala Arg Ala<br>    255                            260                        265 | 997 |
| gtg aaa cct cat cag att ggt ggg atc cgg ttc cta tat gat aac cta<br>Val Lys Pro His Gln Ile Gly Gly Ile Arg Phe Leu Tyr Asp Asn Leu<br>270                        275                        280                        285 | 1045 |
| gtg gag tcc tta gaa agg ttt aag acc agt agt ggc ttt ggc tgt atc<br>Val Glu Ser Leu Glu Arg Phe Lys Thr Ser Ser Gly Phe Gly Cys Ile<br>                290                            295                        300 | 1093 |
| ctg gcc cat agc atg ggc ctg ggg aaa act ctg caa gtg atc tcc ttc<br>Leu Ala His Ser Met Gly Leu Gly Lys Thr Leu Gln Val Ile Ser Phe<br>    305                            310                        315 | 1141 |
| att gat gtc ctt ttc cgc cat act cca gcc aaa aca gtc ctt gcc att<br>Ile Asp Val Leu Phe Arg His Thr Pro Ala Lys Thr Val Leu Ala Ile<br>320                        325                        330 | 1189 |
| gtg ccg gtg aac act ctt cag aat tgg ttg gca gag ttc aac atg tgg<br>Val Pro Val Asn Thr Leu Gln Asn Trp Leu Ala Glu Phe Asn Met Trp<br>                335                            340                        345 | 1237 |
| ctc ccg gct cct gaa gcc ctc cca gcc gac agc aag cct gaa gaa gtc<br>Leu Pro Ala Pro Glu Ala Leu Pro Ala Asp Ser Lys Pro Glu Glu Val<br>350                        355                        360                        365 | 1285 |
| cag cct cgg ttc ttt aaa gtt cat atc ttg aat gat gaa cac aag acg<br>Gln Pro Arg Phe Phe Lys Val His Ile Leu Asn Asp Glu His Lys Thr<br>                370                            375                        380 | 1333 |
| gtg gca tcc cgt gct aaa gtg acg gct gat tgg gtt tca gag ggt gga<br>Val Ala Ser Arg Ala Lys Val Thr Ala Asp Trp Val Ser Glu Gly Gly<br>    385                            390                        395 | 1381 |
| gtg ctg ctg atg ggg tat gag atg tac aga cta ctc aca ctg aag aag<br>Val Leu Leu Met Gly Tyr Glu Met Tyr Arg Leu Leu Thr Leu Lys Lys<br>400                        405                        410 | 1429 |
| tcc tta gcc aca agt agg ccg aag aaa acc aag aaa cgc tct cat ccc<br>Ser Leu Ala Thr Ser Arg Pro Lys Lys Thr Lys Lys Arg Ser His Pro<br>    415                            420                        425 | 1477 |
| gtc atc att gat ctg gat gaa gaa gac cgg cag cag gag ttc cgg aga<br>Val Ile Ile Asp Leu Asp Glu Glu Asp Arg Gln Gln Glu Phe Arg Arg<br>430                        435                        440                        445 | 1525 |
| gag ttt gag aag gcc tta tgc cgc cct ggt cct gat gtg gtg atc tgt<br>Glu Phe Glu Lys Ala Leu Cys Arg Pro Gly Pro Asp Val Val Ile Cys<br>                450                            455                        460 | 1573 |
| gac gag gga cac cgc atc aaa aat tgc caa gcc agc acc tca cag gct<br>Asp Glu Gly His Arg Ile Lys Asn Cys Gln Ala Ser Thr Ser Gln Ala<br>                  465                        470                        475 | 1621 |
| ctg aag aac ata cgt tct cgt cgg cgg gta gtg ctg act ggc tac cct<br>Leu Lys Asn Ile Arg Ser Arg Arg Arg Val Val Leu Thr Gly Tyr Pro<br>        480                            485                        490 | 1669 |
| cta cag aac aac ctc att gag tac tgg tgc atg gtg gac ttt gtg cgc<br>Leu Gln Asn Asn Leu Ile Glu Tyr Trp Cys Met Val Asp Phe Val Arg<br>495                        500                        505 | 1717 |
| cca gat ttc ctt ggt act cgt cag gag ttt agc aac atg ttt gaa cgc<br>Pro Asp Phe Leu Gly Thr Arg Gln Glu Phe Ser Asn Met Phe Glu Arg<br>510                        515                        520                        525 | 1765 |
| cct atc cta aac gga cag tgt att gac agc aca cct cag gat gtc cgc<br>Pro Ile Leu Asn Gly Gln Cys Ile Asp Ser Thr Pro Gln Asp Val Arg<br>                  530                        535                        540 | 1813 |
| ctc atg cgc tac cgg agc cat gtt ttg cac agc ctc ctg gag ggc ttc | 1861 |

-continued

```
                Leu Met Arg Tyr Arg Ser His Val Leu His Ser Leu Leu Glu Gly Phe
                            545                 550                 555 gtg cag agg aga ggc cac act gtg ttg aag att cac ctc cct gcc aaa        1909
Val Gln Arg Arg Gly His Thr Val Leu Lys Ile His Leu Pro Ala Lys
            560                 565                 570 gaa gag aat gtg atc ctg gtg cgg ctt tct cag atc cag cga gat ttg        1957
Glu Glu Asn Val Ile Leu Val Arg Leu Ser Gln Ile Gln Arg Asp Leu
575                 580                 585 tac aca caa ttc atg gac cgt ttc cgg gat tgt ggt acc agt ggc tgg        2005
Tyr Thr Gln Phe Met Asp Arg Phe Arg Asp Cys Gly Thr Ser Gly Trp
590                 595                 600                 605 tta ggg ctg aat cct ctg aag gct ttc tgt gta tgc tgc aag atc tgg        2053
Leu Gly Leu Asn Pro Leu Lys Ala Phe Cys Val Cys Cys Lys Ile Trp
            610                 615                 620 aac cat cct gat gtg ctg tat gaa gcc ctt cag aag gaa aac cta gcc        2101
Asn His Pro Asp Val Leu Tyr Glu Ala Leu Gln Lys Glu Asn Leu Ala
            625                 630                 635 aat gag caa gac cta gat gtg gaa gaa ctt ggc tca gcg ggg acc agt        2149
Asn Glu Gln Asp Leu Asp Val Glu Glu Leu Gly Ser Ala Gly Thr Ser
            640                 645                 650 gcc cgc tgc cca cca cac ggc aca aaa gtc aag gga gaa gat agt gcc        2197
Ala Arg Cys Pro Pro His Gly Thr Lys Val Lys Gly Glu Asp Ser Ala
655                 660                 665 ttg cct tcc tca atg gga gaa gca acc aac agc aag ttc cta cag gga        2245
Leu Pro Ser Ser Met Gly Glu Ala Thr Asn Ser Lys Phe Leu Gln Gly
670                 675                 680                 685 gtt ggc ttt aac cct ttc cag gaa cgg ggc aat aac att gtt aca tat        2293
Val Gly Phe Asn Pro Phe Gln Glu Arg Gly Asn Asn Ile Val Thr Tyr
            690                 695                 700 gag tgg gcc aag gag ctt ctg act aat tat cag act gga gtc ctg gag        2341
Glu Trp Ala Lys Glu Leu Leu Thr Asn Tyr Gln Thr Gly Val Leu Glu
            705                 710                 715 aac tct ccc aag atg gta ctg ctt ttc cac ctg att gaa gaa agc gtg        2389
Asn Ser Pro Lys Met Val Leu Leu Phe His Leu Ile Glu Glu Ser Val
            720                 725                 730 aag ctc ggg gac aag att ctt gta ttt agc cag agc ctt tct acc ttg        2437
Lys Leu Gly Asp Lys Ile Leu Val Phe Ser Gln Ser Leu Ser Thr Leu
            735                 740                 745 gct ctc atc gag gag ttc cta ggg aaa cga gac atg cct tgt ctg cct        2485
Ala Leu Ile Glu Glu Phe Leu Gly Lys Arg Asp Met Pro Cys Leu Pro
750                 755                 760                 765 ggt gcc gag ggg caa gga aca cag aag tgg gtt cga aat gtc agc tac        2533
Gly Ala Glu Gly Gln Gly Thr Gln Lys Trp Val Arg Asn Val Ser Tyr
            770                 775                 780 ttc cgg cta gat ggt agc acc cct gcc ttt gag agg gag cgg ctc att        2581
Phe Arg Leu Asp Gly Ser Thr Pro Ala Phe Glu Arg Glu Arg Leu Ile
            785                 790                 795 aat cag ttc aat gat ccc agc aac ctc acc acc tgg ctg ttc ctt ctc        2629
Asn Gln Phe Asn Asp Pro Ser Asn Leu Thr Thr Trp Leu Phe Leu Leu
            800                 805                 810 tcc aca agg gcc gga tgc ttg ggg gtg aat ctg att ggt gcc aat cga        2677
Ser Thr Arg Ala Gly Cys Leu Gly Val Asn Leu Ile Gly Ala Asn Arg
815                 820                 825 gtg gtg gta ttc gat gct tcc tgg aac cct tgc cat gat gcc cag gca        2725
Val Val Val Phe Asp Ala Ser Trp Asn Pro Cys His Asp Ala Gln Ala
830                 835                 840                 845 gta tgt cgg gta tac cgt tat ggc cag aaa aag ccc tgt cac atc tat        2773
Val Cys Arg Val Tyr Arg Tyr Gly Gln Lys Lys Pro Cys His Ile Tyr
            850                 855                 860
```

```
cga ctc gtg gct gat tat act ctt gag aag aag ata tat gac cgg cag         2821
Arg Leu Val Ala Asp Tyr Thr Leu Glu Lys Lys Ile Tyr Asp Arg Gln
            865                 870                 875 att tcc aag cag ggc atg tca gat cgg gta gtg gat gat cta aat cca         2869
Ile Ser Lys Gln Gly Met Ser Asp Arg Val Val Asp Asp Leu Asn Pro
        880                 885                 890 atg ctg aac ttc acc cgg aag gaa gtg gaa aac ctg ctg cac ttt gtt         2917
Met Leu Asn Phe Thr Arg Lys Glu Val Glu Asn Leu Leu His Phe Val
    895                 900                 905 gag aag gag cca gct ccc caa aca tct ttg gat ata aag ggg atc aag         2965
Glu Lys Glu Pro Ala Pro Gln Thr Ser Leu Asp Ile Lys Gly Ile Lys
910                 915                 920                 925 gag tca gtc ttg caa ctt gcc tgc ctg aag tac cct cac ctc atc acc         3013
Glu Ser Val Leu Gln Leu Ala Cys Leu Lys Tyr Pro His Leu Ile Thr
                930                 935                 940 aag gag cct ttt gag cac gag tca ttg ctc ctc aac cga aaa gat cac         3061
Lys Glu Pro Phe Glu His Glu Ser Leu Leu Leu Asn Arg Lys Asp His
            945                 950                 955 aag ctg acc aaa gct gag aag aaa gca gca aag aaa agc tat gag gag         3109
Lys Leu Thr Lys Ala Glu Lys Lys Ala Ala Lys Lys Ser Tyr Glu Glu
        960                 965                 970 gac aaa cgc aca tca gta ccc tat acc cgc cca tca tat gcg cag tat         3157
Asp Lys Arg Thr Ser Val Pro Tyr Thr Arg Pro Ser Tyr Ala Gln Tyr
    975                 980                 985 tac cct gcc agc gac cag agc ctg acc agc atc cct gcc ttc agt cag         3205
Tyr Pro Ala Ser Asp Gln Ser Leu Thr Ser Ile Pro Ala Phe Ser Gln
990                 995                 1000                1005 agg aac tgg cag cca aca ctg aag ggt gat gaa aag cct gtg gcc             3250
Arg Asn Trp Gln Pro Thr Leu Lys Gly Asp Glu Lys Pro Val Ala
                1010                1015                1020 agc gtt cgt cct gta cag tcc acc ccc att ccc atg atg ccc cgg             3295
Ser Val Arg Pro Val Gln Ser Thr Pro Ile Pro Met Met Pro Arg
            1025                1030                1035 cat gtc cca ctc agt ggt ggt gta agc tct gcc tcc agc aca aat             3340
His Val Pro Leu Ser Gly Gly Val Ser Ser Ala Ser Ser Thr Asn
        1040                1045                1050 aca tcc atg aac ttc cct atc aac tac ttg cag cgg gca gga gtc             3385
Thr Ser Met Asn Phe Pro Ile Asn Tyr Leu Gln Arg Ala Gly Val
    1055                1060                1065 ctt gtg cag aaa gtg gtt acc acg aca gat att gtt atc cct gga             3430
Leu Val Gln Lys Val Val Thr Thr Thr Asp Ile Val Ile Pro Gly
1070                1075                1080 ctc aac agc tcc aca gat gtt cag gca aga atc aat gct ggt gag             3475
Leu Asn Ser Ser Thr Asp Val Gln Ala Arg Ile Asn Ala Gly Glu
                1085                1090                1095 agc atc cac atc atc cga ggg acg aaa ggg aca tac atc cgc acc             3520
Ser Ile His Ile Ile Arg Gly Thr Lys Gly Thr Tyr Ile Arg Thr
            1100                1105                1110 agt gat gga cgc atc ttt gct gtc cgg gcg acc ggc aaa cca aag             3565
Ser Asp Gly Arg Ile Phe Ala Val Arg Ala Thr Gly Lys Pro Lys
        1115                1120                1125 gcc cct gaa gat ggt cgg atg gct gcc tca ggt tcc cag ggg cct             3610
Ala Pro Glu Asp Gly Arg Met Ala Ala Ser Gly Ser Gln Gly Pro
    1130                1135                1140 tct ctt gcg tcc aca agc aat ggc aga cat agt gcc tca tca ccc             3655
Ser Leu Ala Ser Thr Ser Asn Gly Arg His Ser Ala Ser Ser Pro
1145                1150                1155 aaa gcc cct gac ccc gag ggg ctg gcc cgg ccg gtc tct cct gac             3700
Lys Ala Pro Asp Pro Glu Gly Leu Ala Arg Pro Val Ser Pro Asp
                1160                1165                1170
```

```
agc cca gaa atc atc agt gaa ctc cag cag tat gca gat gtg gcc      3745
Ser Pro Glu Ile Ile Ser Glu Leu Gln Gln Tyr Ala Asp Val Ala
            1175                1180                1185 gct gct cgg gaa tcc cgg cag agc tcc cca agc atc agt gct gcc      3790
Ala Ala Arg Glu Ser Arg Gln Ser Ser Pro Ser Ile Ser Ala Ala
            1190                1195                1200 ctg cct ggg ccc ccg ggc cag ctt atg gac aac agc acc att cct      3835
Leu Pro Gly Pro Pro Gly Gln Leu Met Asp Asn Ser Thr Ile Pro
            1205                1210                1215 ggg aca gct ctt gga act gag cca tgc ctt ggg ggt cat tgc ctc      3880
Gly Thr Ala Leu Gly Thr Glu Pro Cys Leu Gly Gly His Cys Leu
            1220                1225                1230 aat agt tcc ctc ttg gtg act ggc cag ccc agt ggt ggc agg cac      3925
Asn Ser Ser Leu Leu Val Thr Gly Gln Pro Ser Gly Gly Arg His
            1235                1240                1245 cca gtg ctg gac tta agg ggc cat aag cga aag ttg gct act ccg      3970
Pro Val Leu Asp Leu Arg Gly His Lys Arg Lys Leu Ala Thr Pro
            1250                1255                1260 tct gtc acc cag gaa tca atc cgt cga cgg tcc agg aag ggc cat      4015
Ser Val Thr Gln Glu Ser Ile Arg Arg Arg Ser Arg Lys Gly His
            1265                1270                1275 ctg cca gcc ccc gtg cag ccc tat gaa cat ggg tat cca gtc tct      4060
Leu Pro Ala Pro Val Gln Pro Tyr Glu His Gly Tyr Pro Val Ser
            1280                1285                1290 ggc ggg ttt gca atg ccg cct gtc tcc tta aat cat aac ctc acc      4105
Gly Gly Phe Ala Met Pro Pro Val Ser Leu Asn His Asn Leu Thr
            1295                1300                1305 acc ccc ttc acc tcc cag gct ggg gag aat tcc cta ttt atg ggc      4150
Thr Pro Phe Thr Ser Gln Ala Gly Glu Asn Ser Leu Phe Met Gly
            1310                1315                1320 agt aat ccc tcc tac tac cag ctg tcc aat ttg ctg gca gat gcc      4195
Ser Asn Pro Ser Tyr Tyr Gln Leu Ser Asn Leu Leu Ala Asp Ala
            1325                1330                1335 cgc ctg gtg ttt cca gtg act act gac cct ctg gtg cca gca ggc      4240
Arg Leu Val Phe Pro Val Thr Thr Asp Pro Leu Val Pro Ala Gly
            1340                1345                1350 cct gtc agt tcc tct tcc acg gct acc tca gtc act gcc agc aac      4285
Pro Val Ser Ser Ser Ser Thr Ala Thr Ser Val Thr Ala Ser Asn
            1355                1360                1365 ccc tcc ttc atg ctc aac ccc tcc gtg cca ggg atg cta ccc agc      4330
Pro Ser Phe Met Leu Asn Pro Ser Val Pro Gly Met Leu Pro Ser
            1370                1375                1380 tat tca ctc cca ttc tca cag cca ctc ctg tcc gag ccc agg atg      4375
Tyr Ser Leu Pro Phe Ser Gln Pro Leu Leu Ser Glu Pro Arg Met
            1385                1390                1395 ttt gcg cct ttc cct tcc ccc ggc ttg ccc agc aac ctt tct cgg      4420
Phe Ala Pro Phe Pro Ser Pro Gly Leu Pro Ser Asn Leu Ser Arg
            1400                1405                1410 ggc gtg tct gtc tac cca ggc tat atg tcc cca cat gca ggc tac      4465
Gly Val Ser Val Tyr Pro Gly Tyr Met Ser Pro His Ala Gly Tyr
            1415                1420                1425 cca gct ggt ggc ctc ctc cgg tcc cag gtg cct cca ttt gac tcg      4510
Pro Ala Gly Gly Leu Leu Arg Ser Gln Val Pro Pro Phe Asp Ser
            1430                1435                1440 cat gag gtg gcg gag gtg ggg ttc agc tcc aat gat gat gag gat      4555
His Glu Val Ala Glu Val Gly Phe Ser Ser Asn Asp Asp Glu Asp
            1445                1450                1455 aaa gat gat gat gtg ata gag gtc act ggg aag tagctaggaa          4598
Lys Asp Asp Asp Val Ile Glu Val Thr Gly Lys
```

-continued

```
                1460              1465
gcccctgcca cctcacttgg ggcccctagg aggttgccca ccaaactgga aggcaatgaa      4658
tctggtcttt ctgaaaatag ggtacttgga gggaaaagaa gacaaaggag agtggttggc      4718
cataatggca ggctctattg ctgttcatta aagaaaaaa gaaaagaccc cagaaactcc       4778
acagagctgt aatagtggga aatcagggac cgaaaacagg gatggggtgt gtggcagcct      4838
gcccttcctt cccgtctttc ttctgctgtc tgcttagatg cccatttgag tgtagaagcg      4898
catatcccat tctgcctttg ggaacgtctc tcccaagaaa tctgcctgag ttacttagtt      4958
tggcctgagg gtggaagaag actgagggcg ggcatgggga gcagattcca cagggagggt      5018
atctcttagg aggtgggaag gaagtgaacc aggccgtgtg tgtgtgtg                   5066
```

<210> SEQ ID NO 2
<211> LENGTH: 1466
<212> TYPE: PRT
<213> ORGANISM: Mus musculus

<400> SEQUENCE: 2

```
Met Ser Asp Glu Ser Ala Ser Gly Ser Asp Pro Asp Leu Asp Pro Asp
1               5                  10                  15

Val Glu Leu Glu Asp Glu Glu Glu Glu Glu Glu Glu Glu Glu Val Ala
            20                  25                  30

Val Glu Glu His Asp Arg Asp Asp Glu Glu Gly Leu Leu Asp Asp Thr
        35                  40                  45

Ser Leu Glu Gly Met Cys Gly Thr Glu His Ala Gln Leu Gly Glu Asp
    50                  55                  60

Gly Gln Arg Pro Pro Arg Cys Thr Ser Thr Thr Ser Ser Gln Ser Glu
65                  70                  75                  80

Pro Ser Glu Gln Leu Arg His Gln Gly Lys Ile Leu Ala Ser Glu Asp
                85                  90                  95

Pro Lys Lys Lys Arg Ala Gln Lys Pro Ser His Met Arg Arg Asn Ile
            100                 105                 110

Arg Lys Leu Leu Arg Glu Asp Gln Leu Glu Pro Val Thr Lys Ala Ala
        115                 120                 125

Gln Gln Glu Glu Leu Glu Arg Arg Lys Arg Leu Glu Gln Gln Arg Lys
    130                 135                 140

Glu Tyr Ala Ala Pro Ile Pro Thr Val Pro Leu Glu Phe Leu Pro Glu
145                 150                 155                 160

Glu Ile Val Leu Arg Ala Ser Asp Gly Pro Gln Leu Pro Pro Arg Val
                165                 170                 175

Leu Ala Gln Glu Val Ile Cys Leu Asp Ser Ser Gly Ser Glu Asp
            180                 185                 190

Glu Lys Ser Ser Arg Asp Glu Val Ile Glu Leu Ser Ser Gly Glu Glu
        195                 200                 205

Asp Thr Leu His Ile Val Asp Ser Ser Glu Ser Val Ser Glu Glu Asp
    210                 215                 220

Glu Glu Glu Glu Lys Gly Gly Thr His Val Asn Asp Ala Leu Asn Gln
225                 230                 235                 240

His Asp Ala Leu Gly Arg Val Leu Val Asn Leu Asn His Pro Pro Glu
                245                 250                 255

Glu Glu Asn Val Phe Leu Ala Pro Gln Leu Ala Arg Ala Val Lys Pro
            260                 265                 270

His Gln Ile Gly Gly Ile Arg Phe Leu Tyr Asp Asn Leu Val Glu Ser
        275                 280                 285
```

```
Leu Glu Arg Phe Lys Thr Ser Ser Gly Phe Gly Cys Ile Leu Ala His
    290                 295                 300

Ser Met Gly Leu Gly Lys Thr Leu Gln Val Ile Ser Phe Ile Asp Val
305                 310                 315                 320

Leu Phe Arg His Thr Pro Ala Lys Thr Val Leu Ala Ile Val Pro Val
                325                 330                 335

Asn Thr Leu Gln Asn Trp Leu Ala Glu Phe Asn Met Trp Leu Pro Ala
                340                 345                 350

Pro Glu Ala Leu Pro Ala Asp Ser Lys Pro Glu Val Gln Pro Arg
                355                 360                 365

Phe Phe Lys Val His Ile Leu Asn Asp Glu His Lys Thr Val Ala Ser
    370                 375                 380

Arg Ala Lys Val Thr Ala Asp Trp Val Ser Glu Gly Val Leu Leu
385                 390                 395                 400

Met Gly Tyr Glu Met Tyr Arg Leu Leu Thr Leu Lys Lys Ser Leu Ala
                405                 410                 415

Thr Ser Arg Pro Lys Lys Thr Lys Lys Arg Ser His Pro Val Ile Ile
                420                 425                 430

Asp Leu Asp Glu Glu Asp Arg Gln Gln Glu Phe Arg Arg Glu Phe Glu
                435                 440                 445

Lys Ala Leu Cys Arg Pro Gly Pro Asp Val Val Ile Cys Asp Glu Gly
    450                 455                 460

His Arg Ile Lys Asn Cys Gln Ala Ser Thr Ser Gln Ala Leu Lys Asn
465                 470                 475                 480

Ile Arg Ser Arg Arg Arg Val Val Leu Thr Gly Tyr Pro Leu Gln Asn
                485                 490                 495

Asn Leu Ile Glu Tyr Trp Cys Met Val Asp Phe Val Arg Pro Asp Phe
                500                 505                 510

Leu Gly Thr Arg Gln Glu Phe Ser Asn Met Phe Glu Arg Pro Ile Leu
                515                 520                 525

Asn Gly Gln Cys Ile Asp Ser Thr Pro Gln Asp Val Arg Leu Met Arg
    530                 535                 540

Tyr Arg Ser His Val Leu His Ser Leu Leu Glu Gly Phe Val Gln Arg
545                 550                 555                 560

Arg Gly His Thr Val Leu Lys Ile His Leu Pro Ala Lys Glu Glu Asn
                565                 570                 575

Val Ile Leu Val Arg Leu Ser Gln Ile Gln Arg Asp Leu Tyr Thr Gln
                580                 585                 590

Phe Met Asp Arg Phe Arg Asp Cys Gly Thr Ser Gly Trp Leu Gly Leu
    595                 600                 605

Asn Pro Leu Lys Ala Phe Cys Val Cys Cys Lys Ile Trp Asn His Pro
610                 615                 620

Asp Val Leu Tyr Glu Ala Leu Gln Lys Glu Asn Leu Ala Asn Glu Gln
625                 630                 635                 640

Asp Leu Asp Val Glu Glu Leu Gly Ser Ala Gly Thr Ser Ala Arg Cys
                645                 650                 655

Pro Pro His Gly Thr Lys Val Lys Gly Glu Asp Ser Ala Leu Pro Ser
                660                 665                 670

Ser Met Gly Glu Ala Thr Asn Ser Lys Phe Leu Gln Gly Val Gly Phe
    675                 680                 685

Asn Pro Phe Gln Glu Arg Gly Asn Asn Ile Val Thr Tyr Glu Trp Ala
    690                 695                 700
```

-continued

```
Lys Glu Leu Leu Thr Asn Tyr Gln Thr Gly Val Leu Glu Asn Ser Pro
705                 710                 715                 720

Lys Met Val Leu Leu Phe His Leu Ile Glu Glu Ser Val Lys Leu Gly
            725                 730                 735

Asp Lys Ile Leu Val Phe Ser Gln Ser Leu Ser Thr Leu Ala Leu Ile
            740                 745                 750

Glu Glu Phe Leu Gly Lys Arg Asp Met Pro Cys Leu Pro Gly Ala Glu
            755                 760                 765

Gly Gln Gly Thr Gln Lys Trp Val Arg Asn Val Ser Tyr Phe Arg Leu
    770                 775                 780

Asp Gly Ser Thr Pro Ala Phe Glu Arg Glu Arg Leu Ile Asn Gln Phe
785                 790                 795                 800

Asn Asp Pro Ser Asn Leu Thr Thr Trp Leu Phe Leu Leu Ser Thr Arg
                805                 810                 815

Ala Gly Cys Leu Gly Val Asn Leu Ile Gly Ala Asn Arg Val Val Val
                820                 825                 830

Phe Asp Ala Ser Trp Asn Pro Cys His Asp Ala Gln Ala Val Cys Arg
            835                 840                 845

Val Tyr Arg Tyr Gly Gln Lys Lys Pro Cys His Ile Tyr Arg Leu Val
850                 855                 860

Ala Asp Tyr Thr Leu Glu Lys Lys Ile Tyr Asp Arg Gln Ile Ser Lys
865                 870                 875                 880

Gln Gly Met Ser Asp Arg Val Val Asp Leu Asn Pro Met Leu Asn
            885                 890                 895

Phe Thr Arg Lys Glu Val Glu Asn Leu Leu His Phe Val Glu Lys Glu
                900                 905                 910

Pro Ala Pro Gln Thr Ser Leu Asp Ile Lys Gly Ile Lys Glu Ser Val
            915                 920                 925

Leu Gln Leu Ala Cys Leu Lys Tyr Pro His Leu Ile Thr Lys Glu Pro
    930                 935                 940

Phe Glu His Glu Ser Leu Leu Leu Asn Arg Lys Asp His Lys Leu Thr
945                 950                 955                 960

Lys Ala Glu Lys Lys Ala Ala Lys Lys Ser Tyr Glu Glu Asp Lys Arg
                965                 970                 975

Thr Ser Val Pro Tyr Thr Arg Pro Ser Tyr Ala Gln Tyr Tyr Pro Ala
            980                 985                 990

Ser Asp Gln Ser Leu Thr Ser Ile Pro Ala Phe Ser Gln Arg Asn Trp
    995                 1000                1005

Gln Pro Thr Leu Lys Gly Asp Glu Lys Pro Val Ala Ser Val Arg
    1010                1015                1020

Pro Val Gln Ser Thr Pro Ile Pro Met Met Pro Arg His Val Pro
    1025                1030                1035

Leu Ser Gly Gly Val Ser Ser Ala Ser Ser Thr Asn Thr Ser Met
    1040                1045                1050

Asn Phe Pro Ile Asn Tyr Leu Gln Arg Ala Gly Val Leu Val Gln
    1055                1060                1065

Lys Val Val Thr Thr Thr Asp Ile Val Ile Pro Gly Leu Asn Ser
    1070                1075                1080

Ser Thr Asp Val Gln Ala Arg Ile Asn Ala Gly Glu Ser Ile His
    1085                1090                1095

Ile Ile Arg Gly Thr Lys Gly Thr Tyr Ile Arg Thr Ser Asp Gly
    1100                1105                1110

Arg Ile Phe Ala Val Arg Ala Thr Gly Lys Pro Lys Ala Pro Glu
```

-continued

Asp Gly Arg Met Ala Ala Ser Gly Ser Gln Gly Pro Ser Leu Ala
    1130                1135                1140

Ser Thr Ser Asn Gly Arg His Ser Ala Ser Ser Pro Lys Ala Pro
    1145                1150                1155

Asp Pro Glu Gly Leu Ala Arg Pro Val Ser Pro Asp Ser Pro Glu
    1160                1165                1170

Ile Ile Ser Glu Leu Gln Gln Tyr Ala Asp Val Ala Ala Ala Arg
    1175                1180                1185

Glu Ser Arg Gln Ser Ser Pro Ser Ile Ser Ala Ala Leu Pro Gly
    1190                1195                1200

Pro Pro Gly Gln Leu Met Asp Asn Ser Thr Ile Pro Gly Thr Ala
    1205                1210                1215

Leu Gly Thr Glu Pro Cys Leu Gly Gly His Cys Leu Asn Ser Ser
    1220                1225                1230

Leu Leu Val Thr Gly Gln Pro Ser Gly Gly Arg His Pro Val Leu
    1235                1240                1245

Asp Leu Arg Gly His Lys Arg Lys Leu Ala Thr Pro Ser Val Thr
    1250                1255                1260

Gln Glu Ser Ile Arg Arg Arg Ser Arg Lys Gly His Leu Pro Ala
    1265                1270                1275

Pro Val Gln Pro Tyr Glu His Gly Tyr Pro Val Ser Gly Gly Phe
    1280                1285                1290

Ala Met Pro Pro Val Ser Leu Asn His Asn Leu Thr Thr Pro Phe
    1295                1300                1305

Thr Ser Gln Ala Gly Glu Asn Ser Leu Phe Met Gly Ser Asn Pro
    1310                1315                1320

Ser Tyr Tyr Gln Leu Ser Asn Leu Leu Ala Asp Ala Arg Leu Val
    1325                1330                1335

Phe Pro Val Thr Thr Asp Pro Leu Val Pro Ala Gly Pro Val Ser
    1340                1345                1350

Ser Ser Ser Thr Ala Thr Ser Val Thr Ala Ser Asn Pro Ser Phe
    1355                1360                1365

Met Leu Asn Pro Ser Val Pro Gly Met Leu Pro Ser Tyr Ser Leu
    1370                1375                1380

Pro Phe Ser Gln Pro Leu Leu Ser Glu Pro Arg Met Phe Ala Pro
    1385                1390                1395

Phe Pro Ser Pro Gly Leu Pro Ser Asn Leu Ser Arg Gly Val Ser
    1400                1405                1410

Val Tyr Pro Gly Tyr Met Ser Pro His Ala Gly Tyr Pro Ala Gly
    1415                1420                1425

Gly Leu Leu Arg Ser Gln Val Pro Pro Phe Asp Ser His Glu Val
    1430                1435                1440

Ala Glu Val Gly Phe Ser Ser Asn Asp Asp Glu Asp Lys Asp Asp
    1445                1450                1455

Asp Val Ile Glu Val Thr Gly Lys
    1460                1465

<210> SEQ ID NO 3
<211> LENGTH: 1703
<212> TYPE: PRT
<213> ORGANISM: Saccharomyces cerevisiae

<400> SEQUENCE: 3

-continued

```
Met Asn Ile Pro Gln Arg Gln Phe Ser Asn Glu Glu Val Asn Arg Cys
1               5                   10                  15

Tyr Leu Arg Trp Gln His Leu Arg Asn Glu His Gly Met Asn Ala Pro
            20                  25                  30

Ser Val Pro Glu Phe Ile Tyr Leu Thr Lys Val Leu Gln Phe Ala Ala
        35                  40                  45

Lys Gln Arg Gln Glu Leu Gln Met Gln Arg Gln Gln Gly Ile Ser
50                  55                  60

Gly Ser Gln Gln Asn Ile Val Pro Asn Ser Ser Asp Gln Ala Glu Leu
65                  70                  75                  80

Pro Asn Asn Ala Ser Ser His Ile Ser Ala Ser Ala Ser Pro His Leu
                85                  90                  95

Ala Pro Asn Met Gln Leu Asn Gly Asn Glu Thr Phe Ser Thr Ser Ala
            100                 105                 110

His Gln Ser Pro Ile Met Gln Thr Gln Met Pro Leu Asn Ser Asn Gly
        115                 120                 125

Gly Asn Asn Met Leu Pro Gln Arg Gln Ser Ser Val Gly Ser Leu Asn
130                 135                 140

Ala Thr Asn Phe Ser Pro Thr Pro Ala Asn Asn Gly Glu Asn Ala Ala
145                 150                 155                 160

Glu Lys Pro Asp Asn Ser Asn His Asn Asn Leu Asn Leu Asn Asn Ser
                165                 170                 175

Glu Leu Gln Pro Gln Asn Arg Ser Leu Gln Glu His Asn Ile Gln Asp
            180                 185                 190

Ser Asn Val Met Pro Gly Ser Gln Ile Asn Ser Pro Met Pro Gln Gln
        195                 200                 205

Ala Gln Met Gln Gln Ala Gln Phe Gln Ala Gln Gln Ala Gln Gln Ala
    210                 215                 220

Gln Gln Ala Gln Gln Ala Gln Ala Gln Ala Arg Leu Gln Gln Gly
225                 230                 235                 240

Arg Arg Leu Pro Met Thr Met Phe Thr Ala Glu Gln Ser Glu Leu Leu
                245                 250                 255

Lys Ala Gln Ile Thr Ser Leu Lys Cys Leu Val Asn Arg Lys Pro Ile
            260                 265                 270

Pro Phe Glu Phe Gln Ala Val Ile Gln Lys Ser Ile Asn His Pro Pro
        275                 280                 285

Asp Phe Lys Arg Met Leu Leu Ser Leu Ser Glu Phe Ala Arg Arg Arg
    290                 295                 300

Gln Pro Thr Asp Gln Asn Asn Gln Ser Asn Leu Asn Gly Gly Asn Asn
305                 310                 315                 320

Thr Gln Gln Pro Gly Thr Asn Ser His Tyr Asn Asn Thr Asn Thr Asp
                325                 330                 335

Asn Val Ser Gly Leu Thr Arg Asn Ala Pro Leu Asp Ser Lys Asp Glu
            340                 345                 350

Asn Phe Ala Ser Val Ser Pro Ala Gly Pro Ser Ser Val His Asn Ala
        355                 360                 365

Lys Asn Gly Thr Leu Asp Lys Asn Ser Gln Thr Val Ser Gly Thr Pro
    370                 375                 380

Ile Thr Gln Thr Glu Ser Lys Lys Glu Glu Asn Glu Thr Ile Ser Asn
385                 390                 395                 400

Val Ala Lys Thr Ala Pro Asn Ser Asn Lys Thr His Thr Glu Gln Asn
                405                 410                 415

Asn Pro Pro Lys Pro Gln Lys Pro Val Pro Leu Asn Val Leu Gln Asp
```

-continued

```
                420                 425                 430
Gln Tyr Lys Glu Gly Ile Lys Val Val Asp Ile Asp Pro Asp Met
            435                 440                 445
Met Val Asp Ser Phe Thr Met Pro Asn Ile Ser His Ser Asn Ile Asp
450                 455                 460
Tyr Gln Thr Leu Leu Ala Asn Ser Asp His Ala Lys Phe Thr Ile Glu
465                 470                 475                 480
Pro Gly Val Leu Pro Val Gly Ile Asp Thr His Thr Ala Thr Asp Ile
                485                 490                 495
Tyr Gln Thr Leu Ile Ala Leu Asn Leu Asp Thr Thr Val Asn Asp Cys
                500                 505                 510
Leu Asp Lys Leu Leu Asn Asp Glu Cys Thr Glu Ser Thr Arg Glu Asn
            515                 520                 525
Ala Leu Tyr Asp Tyr Tyr Ala Leu Gln Leu Leu Pro Leu Gln Lys Ala
        530                 535                 540
Val Arg Gly His Val Leu Gln Phe Glu Trp His Gln Asn Ser Leu Leu
545                 550                 555                 560
Thr Asn Thr His Pro Asn Phe Leu Ser Lys Ile Arg Asn Ile Asn Val
                565                 570                 575
Gln Asp Ala Leu Leu Thr Asn Gln Leu Tyr Lys Asn His Glu Leu Leu
            580                 585                 590
Lys Leu Glu Arg Lys Lys Thr Glu Ala Val Ala Arg Leu Lys Ser Met
        595                 600                 605
Asn Lys Ser Ala Ile Asn Gln Tyr Asn Arg Arg Gln Asp Lys Lys Asn
    610                 615                 620
Lys Arg Leu Lys Phe Gly His Arg Leu Ile Ala Thr His Thr Asn Leu
625                 630                 635                 640
Glu Arg Asp Glu Gln Lys Arg Ala Glu Lys Ala Lys Glu Arg Leu
                645                 650                 655
Gln Ala Leu Lys Ala Asn Asp Glu Glu Ala Tyr Ile Lys Leu Leu Asp
            660                 665                 670
Gln Thr Lys Asp Thr Arg Ile Thr His Leu Leu Arg Gln Thr Asn Ala
        675                 680                 685
Phe Leu Asp Ser Leu Thr Arg Ala Val Lys Asp Gln Gln Lys Tyr Thr
    690                 695                 700
Lys Glu Met Ile Asp Ser His Ile Lys Glu Ala Ser Glu Val Asp
705                 710                 715                 720
Asp Leu Ser Met Val Pro Lys Met Lys Asp Glu Glu Tyr Asp Asp Asp
                725                 730                 735
Asp Asp Asn Ser Asn Val Asp Tyr Tyr Asn Val Ala His Arg Ile Lys
            740                 745                 750
Glu Asp Ile Lys Lys Gln Pro Ser Ile Leu Val Gly Gly Thr Leu Lys
        755                 760                 765
Asp Tyr Gln Ile Lys Gly Leu Gln Trp Met Val Ser Leu Phe Asn Asn
    770                 775                 780
His Leu Asn Gly Ile Leu Ala Asp Glu Met Gly Leu Gly Lys Thr Ile
785                 790                 795                 800
Gln Thr Ile Ser Leu Leu Thr Tyr Leu Tyr Glu Met Lys Asn Ile Arg
                805                 810                 815
Gly Pro Tyr Leu Val Ile Val Pro Leu Ser Thr Leu Ser Asn Trp Ser
            820                 825                 830
Ser Glu Phe Ala Lys Trp Ala Pro Thr Leu Arg Thr Ile Ser Phe Lys
        835                 840                 845
```

-continued

```
Gly Ser Pro Asn Glu Arg Lys Ala Lys Gln Ala Lys Ile Arg Ala Gly
    850                 855                 860
Glu Phe Asp Val Val Leu Thr Thr Phe Glu Tyr Ile Ile Lys Glu Arg
865                 870                 875                 880
Ala Leu Leu Ser Lys Val Lys Trp Val His Met Ile Ile Asp Glu Gly
                885                 890                 895
His Arg Met Lys Asn Ala Gln Ser Lys Leu Ser Leu Thr Leu Asn Thr
            900                 905                 910
His Tyr His Ala Asp Tyr Arg Leu Ile Leu Thr Gly Thr Pro Leu Gln
            915                 920                 925
Asn Asn Leu Pro Glu Leu Trp Ala Leu Leu Asn Phe Val Leu Pro Lys
        930                 935                 940
Ile Phe Asn Ser Val Lys Ser Phe Asp Glu Trp Phe Asn Thr Pro Phe
945                 950                 955                 960
Ala Asn Thr Gly Gly Gln Asp Lys Ile Glu Leu Ser Glu Glu Glu Thr
                965                 970                 975
Leu Leu Val Ile Arg Arg Leu His Lys Val Leu Arg Pro Phe Leu Leu
            980                 985                 990
Arg Arg Leu Lys Lys Asp Val Glu  Lys Glu Leu Pro Asp  Lys Val Glu
            995                 1000                1005
Lys Val  Val Lys Cys Lys Met  Ser Ala Leu Gln Gln  Ile Met Tyr
    1010                1015                1020
Gln Gln  Met Leu Lys Tyr Arg  Arg Leu Phe Ile Gly  Asp Gln Asn
    1025                1030                1035
Asn Lys  Lys Met Val Gly Leu  Arg Gly Phe Asn Asn  Gln Ile Met
    1040                1045                1050
Gln Leu  Lys Lys Ile Cys Asn  His Pro Phe Val Phe  Glu Glu Val
    1055                1060                1065
Glu Asp  Gln Ile Asn Pro Thr  Arg Glu Thr Asn Asp  Asp Ile Trp
    1070                1075                1080
Arg Val  Ala Gly Lys Phe Glu  Leu Leu Asp Arg Ile  Leu Pro Lys
    1085                1090                1095
Leu Lys  Ala Thr Gly His Arg  Val Leu Ile Phe Phe  Gln Met Thr
    1100                1105                1110
Gln Ile  Met Asp Ile Met Glu  Asp Phe Leu Arg Tyr  Ile Asn Ile
    1115                1120                1125
Lys Tyr  Leu Arg Leu Asp Gly  His Thr Lys Ser Asp  Glu Arg Ser
    1130                1135                1140
Glu Leu  Leu Arg Leu Phe Asn  Ala Pro Asp Ser Glu  Tyr Leu Cys
    1145                1150                1155
Phe Ile  Leu Ser Thr Arg Ala  Gly Gly Leu Gly Leu  Asn Leu Gln
    1160                1165                1170
Thr Ala  Asp Thr Val Ile Ile  Phe Asp Thr Asp Trp  Asn Pro His
    1175                1180                1185
Gln Asp  Leu Gln Ala Gln Asp  Arg Ala His Arg Ile  Gly Gln Lys
    1190                1195                1200
Asn Glu  Val Arg Ile Leu Arg  Leu Ile Thr Thr Asn  Ser Val Glu
    1205                1210                1215
Glu Val  Ile Leu Glu Arg Ala  Tyr Lys Lys Leu Asp  Ile Asp Gly
    1220                1225                1230
Lys Val  Ile Gln Ala Gly Lys  Phe Asp Asn Lys Ser  Thr Ser Glu
    1235                1240                1245
```

-continued

```
Glu Gln Glu Ala Leu Leu Arg Ser Leu Leu Asp Ala Glu Glu Glu
    1250                1255                1260
Arg Arg Lys Lys Arg Glu Ser Gly Val Glu Glu Glu Glu Glu Leu
    1265                1270                1275
Lys Asp Ser Glu Ile Asn Glu Ile Leu Ala Arg Asn Asp Glu Glu
    1280                1285                1290
Met Ala Val Leu Thr Arg Met Asp Glu Asp Arg Ser Lys Lys Glu
    1295                1300                1305
Glu Glu Leu Gly Val Lys Ser Arg Leu Leu Glu Lys Ser Glu Leu
    1310                1315                1320
Pro Asp Ile Tyr Ser Arg Asp Ile Gly Ala Glu Leu Lys Arg Glu
    1325                1330                1335
Glu Ser Glu Ser Ala Ala Val Tyr Asn Gly Arg Gly Ala Arg Glu
    1340                1345                1350
Arg Lys Thr Ala Thr Tyr Asn Asp Asn Met Ser Glu Glu Gln Trp
    1355                1360                1365
Leu Arg Gln Phe Glu Val Ser Asp Asp Glu Lys Asn Asp Lys Gln
    1370                1375                1380
Ala Arg Lys Gln Arg Thr Lys Lys Glu Asp Lys Ser Glu Ala Ile
    1385                1390                1395
Asp Gly Asn Gly Glu Ile Lys Gly Glu Asn Ile Asp Ala Asp Asn
    1400                1405                1410
Asp Gly Pro Arg Ile Asn Asn Ile Ser Ala Glu Asp Arg Ala Asp
    1415                1420                1425
Thr Asp Leu Ala Met Asn Asp Asp Phe Leu Ser Lys Lys Arg
    1430                1435                1440
Lys Ala Gly Arg Pro Arg Gly Arg Pro Lys Lys Val Lys Leu Glu
    1445                1450                1455
Gly Ser Glu Asn Ser Glu Pro Pro Ala Leu Glu Ser Ser Pro Val
    1460                1465                1470
Thr Gly Asp Asn Ser Pro Ser Glu Asp Phe Met Asp Ile Pro Lys
    1475                1480                1485
Pro Arg Thr Ala Gly Lys Thr Ser Val Lys Ser Ala Arg Thr Ser
    1490                1495                1500
Thr Arg Gly Arg Gly Arg Gly Arg Gly Arg Gly Arg Gly Arg Gly
    1505                1510                1515
Arg Gly Arg Gly Arg Pro Pro Lys Ala Arg Asn Gly Leu Asp Tyr
    1520                1525                1530
Val Arg Thr Pro Ala Ala Ala Thr Ser Pro Ile Asp Ile Arg Glu
    1535                1540                1545
Lys Val Ala Lys Gln Ala Leu Asp Leu Tyr His Phe Ala Leu Asn
    1550                1555                1560
Tyr Glu Asn Glu Ala Gly Arg Lys Leu Ser Asp Ile Phe Leu Ser
    1565                1570                1575
Lys Pro Ser Lys Ala Leu Tyr Pro Asp Tyr Tyr Met Ile Ile Lys
    1580                1585                1590
Tyr Pro Val Ala Phe Asp Asn Ile Asn Thr His Ile Glu Thr Leu
    1595                1600                1605
Ala Tyr Asn Ser Leu Lys Glu Thr Leu Gln Asp Phe His Leu Ile
    1610                1615                1620
Phe Ser Asn Ala Arg Ile Tyr Asn Thr Glu Gly Ser Val Val Tyr
    1625                1630                1635
Glu Asp Ser Leu Glu Leu Glu Lys Val Val Thr Lys Lys Tyr Cys
```

-continued

```
               1640                1645                1650
    Glu Ile Met Gly Asp Asn Ser Gln Leu Asp Phe Thr Glu Phe Asp
    1655                1660                1665
    Glu Gln Tyr Gly Thr Arg Pro Leu Val Leu Pro Pro Val Val Thr
    1670                1675                1680
    Ser Ser Val Ala Glu Ser Phe Thr Asp Glu Ala Asp Ser Ser Met
    1685                1690                1695
    Thr Glu Ala Ser Val
    1700

<210> SEQ ID NO 4
<211> LENGTH: 1647
<212> TYPE: PRT
<213> ORGANISM: Homo sapiens

<400> SEQUENCE: 4

Met Ser Thr Pro Asp Pro Pro Leu Gly Gly Thr Pro Arg Pro Gly Pro
1               5                   10                  15
Ser Pro Gly Pro Gly Pro Ser Pro Gly Ala Met Leu Gly Pro Ser Pro
                20                  25                  30
Gly Pro Ser Pro Gly Ser Ala His Ser Met Met Gly Pro Ser Pro Gly
            35                  40                  45
Pro Pro Ser Ala Gly His Pro Ile Pro Thr Gln Gly Pro Gly Gly Tyr
        50                  55                  60
Pro Gln Asp Asn Met His Gln Met His Lys Pro Met Glu Ser Met His
65                  70                  75                  80
Glu Lys Gly Met Ser Asp Asp Pro Arg Tyr Asn Gln Met Lys Gly Met
                85                  90                  95
Gly Met Arg Ser Gly Gly His Ala Gly Met Gly Pro Pro Ser Pro
            100                 105                 110
Met Asp Gln His Ser Gln Gly Tyr Pro Ser Pro Leu Gly Gly Ser Glu
        115                 120                 125
His Ala Ser Ser Pro Val Pro Ala Ser Gly Pro Ser Ser Gly Pro Gln
    130                 135                 140
Met Ser Ser Gly Pro Gly Gly Ala Pro Leu Asp Gly Ala Asp Pro Gln
145                 150                 155                 160
Ala Leu Gly Gln Gln Asn Arg Gly Pro Thr Pro Phe Asn Gln Asn Gln
                165                 170                 175
Leu His Gln Leu Arg Ala Gln Ile Met Ala Tyr Lys Met Leu Ala Arg
            180                 185                 190
Gly Gln Pro Leu Pro Asp His Leu Gln Met Ala Val Gln Gly Lys Arg
        195                 200                 205
Pro Met Pro Gly Met Gln Gln Met Pro Thr Leu Pro Pro Pro Ser
    210                 215                 220
Val Ser Ala Thr Gly Pro Gly Pro Gly Pro Gly Pro Gly Pro Gly Pro
225                 230                 235                 240
Gly Pro Gly Pro Ala Pro Pro Asn Tyr Ser Arg Pro His Gly Met Gly
                245                 250                 255
Gly Pro Asn Met Pro Pro Pro Gly Pro Ser Gly Val Pro Pro Gly Met
            260                 265                 270
Pro Gly Gln Pro Pro Gly Gly Pro Pro Lys Pro Trp Pro Glu Gly Pro
        275                 280                 285
Met Ala Asn Ala Ala Ala Pro Thr Ser Thr Pro Gln Lys Leu Ile Pro
    290                 295                 300
```

```
Pro Gln Pro Thr Gly Arg Pro Ser Pro Ala Pro Pro Ala Val Pro Pro
305                 310                 315                 320

Ala Ala Ser Pro Val Met Pro Pro Gln Thr Gln Ser Pro Gly Gln Pro
            325                 330                 335

Ala Gln Pro Ala Pro Met Val Pro Leu His Gln Lys Gln Ser Arg Ile
            340                 345                 350

Thr Pro Ile Gln Lys Pro Arg Gly Leu Asp Pro Val Glu Ile Leu Gln
            355                 360                 365

Glu Arg Glu Tyr Arg Leu Gln Ala Arg Ile Ala His Arg Ile Gln Glu
370                 375                 380

Leu Glu Asn Leu Pro Gly Ser Leu Ala Gly Asp Leu Arg Thr Lys Ala
385                 390                 395                 400

Thr Ile Glu Leu Lys Ala Leu Arg Leu Leu Asn Phe Gln Arg Gln Leu
                405                 410                 415

Arg Gln Glu Val Val Cys Met Arg Arg Asp Thr Ala Leu Glu Thr
                420                 425                 430

Ala Leu Asn Ala Lys Ala Tyr Lys Arg Ser Lys Arg Gln Ser Leu Arg
            435                 440                 445

Glu Ala Arg Ile Thr Glu Lys Leu Glu Lys Gln Gln Lys Ile Glu Gln
450                 455                 460

Glu Arg Lys Arg Arg Gln Lys His Gln Glu Tyr Leu Asn Ser Ile Leu
465                 470                 475                 480

Gln His Ala Lys Asp Phe Lys Glu Tyr His Arg Ser Val Thr Gly Lys
                485                 490                 495

Ile Gln Lys Leu Thr Lys Ala Val Ala Thr Tyr His Ala Asn Thr Glu
            500                 505                 510

Arg Glu Gln Lys Lys Glu Asn Glu Arg Ile Glu Lys Glu Arg Met Arg
            515                 520                 525

Arg Leu Met Ala Glu Asp Glu Glu Gly Tyr Arg Lys Leu Ile Asp Gln
530                 535                 540

Lys Lys Asp Lys Arg Leu Ala Tyr Leu Leu Gln Gln Thr Asp Glu Tyr
545                 550                 555                 560

Val Ala Asn Leu Thr Glu Leu Val Pro Gln His Lys Ala Ala Gln Val
                565                 570                 575

Ala Lys Glu Lys Lys Lys Lys Lys Lys Lys Lys Ala Glu Asn Ala
            580                 585                 590

Glu Gly Gln Thr Pro Ala Ile Gly Pro Asp Gly Glu Pro Leu Asp Glu
            595                 600                 605

Thr Ser Gln Met Ser Asp Leu Pro Val Lys Val Ile His Val Glu Ser
    610                 615                 620

Gly Lys Ile Leu Thr Gly Thr Asp Ala Pro Lys Ala Gly Gln Leu Glu
625                 630                 635                 640

Ala Trp Leu Glu Met Asn Pro Gly Tyr Glu Val Ala Pro Arg Ser Asp
                645                 650                 655

Ser Glu Glu Ser Gly Ser Glu Glu Glu Glu Glu Glu Glu Glu Glu Glu
            660                 665                 670

Gln Pro Gln Ala Ala Gln Pro Pro Thr Leu Pro Val Glu Glu Lys Lys
    675                 680                 685

Lys Ile Pro Asp Pro Asp Ser Asp Asp Val Ser Glu Val Asp Ala Arg
            690                 695                 700

His Ile Ile Glu Asn Ala Lys Gln Asp Val Asp Asp Glu Tyr Gly Val
705                 710                 715                 720

Ser Gln Ala Leu Ala Arg Gly Leu Gln Ser Tyr Tyr Ala Val Ala His
```

-continued

```
                725                 730                 735
Ala Val Thr Glu Arg Val Asp Lys Gln Ser Ala Leu Met Val Asn Gly
                    740                 745                 750

Val Leu Lys Gln Tyr Gln Ile Lys Gly Leu Glu Trp Leu Val Ser Leu
            755                 760                 765

Tyr Asn Asn Asn Leu Asn Gly Ile Leu Ala Asp Glu Met Gly Leu Gly
    770                 775                 780

Lys Thr Ile Gln Thr Ile Ala Leu Ile Thr Tyr Leu Met Glu His Lys
785                 790                 795                 800

Arg Ile Asn Gly Pro Phe Leu Ile Ile Val Pro Leu Ser Thr Leu Ser
                805                 810                 815

Asn Trp Ala Tyr Glu Phe Asp Lys Trp Ala Pro Ser Val Val Lys Val
                820                 825                 830

Ser Tyr Lys Gly Ser Pro Ala Ala Arg Arg Ala Phe Val Pro Gln Leu
            835                 840                 845

Arg Ser Gly Lys Phe Asn Val Leu Leu Thr Thr Tyr Glu Tyr Ile Ile
    850                 855                 860

Lys Asp Lys His Ile Leu Ala Lys Ile Arg Trp Lys Tyr Met Ile Val
865                 870                 875                 880

Asp Glu Gly His Arg Met Lys Asn His His Cys Lys Leu Thr Gln Val
                885                 890                 895

Leu Asn Thr His Tyr Val Ala Pro Arg Arg Leu Leu Leu Thr Gly Thr
                900                 905                 910

Pro Leu Gln Asn Lys Leu Pro Glu Leu Trp Ala Leu Leu Asn Phe Leu
            915                 920                 925

Leu Pro Thr Ile Phe Lys Ser Cys Ser Thr Phe Glu Gln Trp Phe Asn
    930                 935                 940

Ala Pro Phe Ala Met Thr Gly Glu Lys Val Asp Leu Asn Glu Glu Glu
945                 950                 955                 960

Thr Ile Leu Ile Ile Arg Arg Leu His Lys Val Leu Arg Pro Phe Leu
                965                 970                 975

Leu Arg Arg Leu Lys Lys Glu Val Glu Ala Gln Leu Pro Glu Lys Val
            980                 985                 990

Glu Tyr Val Ile Lys Cys Asp Met Ser Ala Leu Gln Arg Val Leu Tyr
    995                1000                1005

Arg His Met Gln Ala Lys Gly Val Leu Leu Thr Asp Gly Ser Glu
    1010                1015                1020

Lys Asp Lys Lys Gly Lys Gly Gly Thr Lys Thr Leu Met Asn Thr
    1025                1030                1035

Ile Met Gln Leu Arg Lys Ile Cys Asn His Pro Tyr Met Phe Gln
    1040                1045                1050

His Ile Glu Glu Ser Phe Ser Glu His Leu Gly Phe Thr Gly Gly
    1055                1060                1065

Ile Val Gln Gly Leu Asp Leu Tyr Arg Ala Ser Gly Lys Phe Glu
    1070                1075                1080

Leu Leu Asp Arg Ile Leu Pro Lys Leu Arg Ala Thr Asn His Lys
    1085                1090                1095

Val Leu Leu Phe Cys Gln Met Thr Ser Leu Met Thr Ile Met Glu
    1100                1105                1110

Asp Tyr Phe Ala Tyr Arg Gly Phe Lys Tyr Leu Arg Leu Asp Gly
    1115                1120                1125

Thr Thr Lys Ala Glu Asp Arg Gly Met Leu Leu Lys Thr Phe Asn
    1130                1135                1140
```

-continued

```
Glu Pro Gly Ser Glu Tyr Phe Ile Phe Leu Leu Ser Thr Arg Ala
    1145                1150                1155
Gly Gly Leu Gly Leu Asn Leu Gln Ser Ala Asp Thr Val Ile Ile
    1160                1165                1170
Phe Asp Ser Asp Trp Asn Pro His Gln Asp Leu Gln Ala Gln Asp
    1175                1180                1185
Arg Ala His Arg Ile Gly Gln Gln Asn Glu Val Arg Val Leu Arg
    1190                1195                1200
Leu Cys Thr Val Asn Ser Val Glu Glu Lys Ile Leu Ala Ala Ala
    1205                1210                1215
Lys Tyr Lys Leu Asn Val Asp Gln Lys Val Ile Gln Ala Gly Met
    1220                1225                1230
Phe Asp Gln Lys Ser Ser Ser His Glu Arg Arg Ala Phe Leu Gln
    1235                1240                1245
Ala Ile Leu Glu His Glu Glu Gln Asp Glu Ser Arg His Cys Ser
    1250                1255                1260
Thr Gly Ser Gly Ser Ala Ser Phe Ala His Thr Ala Pro Pro Pro
    1265                1270                1275
Ala Gly Val Asn Pro Asp Leu Glu Glu Pro Pro Leu Lys Glu Glu
    1280                1285                1290
Asp Glu Val Pro Asp Asp Glu Thr Val Asn Gln Met Ile Ala Arg
    1295                1300                1305
His Glu Glu Glu Phe Asp Leu Phe Met Arg Met Asp Leu Asp Arg
    1310                1315                1320
Arg Arg Glu Glu Ala Arg Asn Pro Lys Arg Lys Pro Arg Leu Met
    1325                1330                1335
Glu Glu Asp Glu Leu Pro Ser Trp Ile Ile Lys Asp Asp Ala Glu
    1340                1345                1350
Val Glu Arg Leu Thr Cys Glu Glu Glu Glu Lys Met Phe Gly
    1355                1360                1365
Arg Gly Ser Arg His Arg Lys Glu Val Asp Tyr Ser Asp Ser Leu
    1370                1375                1380
Thr Glu Lys Gln Trp Leu Lys Ala Ile Glu Glu Gly Thr Leu Glu
    1385                1390                1395
Glu Ile Glu Glu Glu Val Arg Gln Lys Lys Ser Ser Arg Lys Arg
    1400                1405                1410
Lys Arg Asp Ser Asp Ala Gly Ser Ser Thr Pro Thr Thr Ser Thr
    1415                1420                1425
Arg Ser Arg Asp Lys Asp Asp Glu Ser Lys Lys Gln Lys Lys Arg
    1430                1435                1440
Gly Arg Pro Pro Ala Glu Lys Leu Ser Pro Asn Pro Pro Asn Leu
    1445                1450                1455
Thr Lys Lys Met Lys Lys Ile Val Asp Ala Val Ile Lys Tyr Lys
    1460                1465                1470
Asp Ser Ser Ser Gly Arg Gln Leu Ser Glu Val Phe Ile Gln Leu
    1475                1480                1485
Pro Ser Arg Lys Glu Leu Pro Glu Tyr Tyr Glu Leu Ile Arg Lys
    1490                1495                1500
Pro Val Asp Phe Lys Lys Ile Lys Glu Arg Ile Arg Asn His Lys
    1505                1510                1515
Tyr Arg Ser Leu Asn Asp Leu Glu Lys Asp Val Met Leu Leu Cys
    1520                1525                1530
```

-continued

```
Gln Asn Ala Gln Thr Phe Asn Leu Glu Gly Ser Leu Ile Tyr Glu
    1535                1540                1545

Asp Ser Ile Val Leu Gln Ser Val Phe Thr Ser Val Arg Gln Lys
    1550                1555                1560

Ile Glu Lys Glu Asp Asp Ser Glu Gly Glu Glu Ser Glu Glu Glu
    1565                1570                1575

Glu Glu Gly Glu Glu Gly Ser Glu Ser Glu Ser Arg Ser Val
    1580                1585                1590

Lys Val Lys Ile Lys Leu Gly Arg Lys Glu Lys Ala Gln Asp Arg
    1595                1600                1605

Leu Lys Gly Gly Arg Arg Arg Pro Ser Arg Gly Ser Arg Ala Lys
    1610                1615                1620

Pro Val Val Ser Asp Asp Asp Ser Glu Glu Glu Gln Glu Glu Asp
    1625                1630                1635

Arg Ser Gly Ser Gly Ser Glu Glu Asp
    1640                1645

<210> SEQ ID NO 5
<211> LENGTH: 1867
<212> TYPE: PRT
<213> ORGANISM: Saccharomyces cerevisiae

<400> SEQUENCE: 5

Met Thr Ser Arg Val Ser Arg Leu Asp Arg Gln Val Ile Leu Ile Glu
1               5                   10                  15

Thr Gly Ser Thr Gln Val Val Arg Asn Met Ala Ala Asp Gln Met Gly
                20                  25                  30

Asp Leu Ala Lys Gln His Pro Glu Asp Ile Leu Ser Leu Leu Ser Arg
            35                  40                  45

Val Tyr Pro Phe Leu Leu Val Lys Lys Trp Glu Thr Arg Val Thr Ala
        50                  55                  60

Ala Arg Ala Val Gly Gly Ile Val Ala His Ala Pro Ser Trp Asp Pro
65                  70                  75                  80

Asn Glu Ser Asp Leu Val Gly Gly Thr Asn Glu Gly Ser Pro Leu Asp
                85                  90                  95

Asn Ala Gln Val Lys Leu Glu His Glu Met Lys Ile Lys Leu Glu Glu
            100                 105                 110

Ala Thr Gln Asn Asn Gln Leu Asn Leu Leu Gln Glu Asp His His Leu
        115                 120                 125

Ser Ser Leu Ser Asp Trp Lys Leu Asn Glu Ile Leu Lys Ser Gly Lys
    130                 135                 140

Val Leu Leu Ala Ser Ser Met Asn Asp Tyr Asn Val Leu Gly Lys Ala
145                 150                 155                 160

Asp Asp Asn Ile Arg Lys Gln Ala Lys Thr Asp Asp Ile Lys Gln Glu
                165                 170                 175

Thr Ser Met Leu Asn Ala Ser Asp Lys Ala Asn Glu Asn Lys Ser Asn
            180                 185                 190

Ala Asn Lys Lys Ser Ala Arg Met Leu Ala Met Ala Arg Arg Lys Lys
        195                 200                 205

Lys Met Ser Ala Lys Asn Thr Pro Lys His Pro Val Asp Ile Thr Glu
    210                 215                 220

Ser Ser Val Ser Lys Thr Leu Leu Asn Gly Lys Asn Met Thr Asn Ser
225                 230                 235                 240

Ala Ala Ser Leu Ala Thr Ser Pro Thr Ser Asn Gln Leu Asn Pro Lys
                245                 250                 255
```

-continued

```
Leu Glu Ile Thr Glu Gln Ala Asp Glu Ser Lys Leu Met Ile Glu Ser
            260                 265                 270
Thr Val Arg Pro Leu Leu Glu Gln His Glu Ile Val Ala Gly Leu Val
            275                 280                 285
Trp Gln Phe Gln Gly Ile Tyr Glu Leu Leu Asp Asn Leu Met Ser
            290                 295                 300
Glu Asn Trp Glu Ile Arg His Gly Ala Ala Leu Gly Leu Arg Glu Leu
305                         310                 315                 320
Val Lys Lys His Ala Tyr Gly Val Ser Arg Val Lys Gly Asn Thr Arg
                    325                 330                 335
Glu Glu Asn Asn Leu Arg Asn Ser Arg Ser Leu Glu Asp Leu Ala Ser
                340                 345                 350
Arg Leu Leu Thr Val Phe Ala Leu Asp Arg Phe Gly Asp Tyr Val Tyr
                355                 360                 365
Asp Thr Val Val Ala Pro Val Arg Glu Ser Val Ala Gln Thr Leu Ala
            370                 375                 380
Ala Leu Leu Ile His Leu Asp Ser Thr Leu Ser Ile Lys Ile Phe Asn
385                         390                 395                 400
Cys Leu Glu Gln Leu Val Leu Gln Asp Pro Leu Gln Thr Gly Leu Pro
                    405                 410                 415
Asn Lys Ile Trp Glu Ala Thr His Gly Gly Leu Leu Gly Ile Arg Tyr
                420                 425                 430
Phe Val Ser Ile Lys Thr Asn Phe Leu Phe Ala His Gly Leu Leu Glu
                435                 440                 445
Asn Val Val Arg Ile Val Leu Tyr Gly Leu Asn Gln Ser Asp Asp Asp
450                         455                 460
Val Gln Ser Val Ala Ala Ser Ile Leu Thr Pro Ile Thr Ser Glu Phe
465                         470                 475                 480
Val Lys Leu Asn Asn Ser Thr Ile Glu Ile Leu Val Thr Thr Ile Trp
                485                 490                 495
Ser Leu Leu Ala Arg Leu Asp Asp Asp Ile Ser Ser Ser Val Gly Ser
                500                 505                 510
Ile Met Asp Leu Leu Ala Lys Leu Cys Asp His Gln Glu Val Leu Asp
                515                 520                 525
Ile Leu Lys Asn Lys Ala Leu Glu His Pro Ser Glu Trp Ser Phe Lys
            530                 535                 540
Ser Leu Val Pro Lys Leu Tyr Pro Phe Leu Arg His Ser Ile Ser Ser
545                         550                 555                 560
Val Arg Arg Ala Val Leu Asn Leu Leu Ile Ala Phe Leu Ser Ile Lys
                    565                 570                 575
Asp Asp Ser Thr Lys Asn Trp Leu Asn Gly Lys Val Phe Arg Leu Val
                580                 585                 590
Phe Gln Asn Ile Leu Leu Glu Gln Asn Pro Glu Leu Leu Gln Leu Ser
            595                 600                 605
Phe Asp Val Tyr Val Ala Leu Leu Glu His Tyr Lys Val Lys His Thr
            610                 615                 620
Glu Lys Thr Leu Asp His Val Phe Ser Lys His Leu Gln Pro Ile Leu
625                         630                 635                 640
His Leu Leu Asn Thr Pro Val Gly Glu Lys Gly Lys Asn Tyr Ala Met
                    645                 650                 655
Glu Ser Gln Tyr Ile Leu Lys Pro Ser Gln His Tyr Gln Leu His Pro
                660                 665                 670
```

```
Glu Lys Lys Arg Ser Ile Ser Glu Thr Thr Asp Ser Asp Ile Pro
        675                 680                 685

Ile Pro Lys Asn Asn Glu His Ile Asn Ile Asp Ala Pro Met Ile Ala
        690                 695                 700

Gly Asp Ile Thr Leu Leu Gly Leu Asp Val Ile Leu Asn Thr Arg Ile
705                 710                 715                 720

Met Gly Ala Lys Ala Phe Ala Leu Thr Leu Ser Met Phe Gln Asp Ser
                725                 730                 735

Thr Leu Gln Ser Phe Phe Thr Asn Val Leu Val Arg Cys Leu Glu Leu
            740                 745                 750

Pro Phe Ser Thr Pro Arg Met Leu Ala Gly Ile Ile Val Ser Gln Phe
        755                 760                 765

Cys Ser Ser Trp Leu Gln Lys His Pro Glu Gly Glu Lys Leu Pro Ser
770                 775                 780

Phe Val Ser Glu Ile Phe Ser Pro Val Met Asn Lys Gln Leu Leu Asn
785                 790                 795                 800

Arg Asp Glu Phe Pro Val Phe Arg Glu Leu Val Pro Ser Leu Lys Ala
                805                 810                 815

Leu Arg Thr Gln Cys Gln Ser Leu Leu Ala Thr Phe Val Asp Val Gly
            820                 825                 830

Met Leu Pro Gln Tyr Lys Leu Pro Asn Val Ala Ile Val Val Gln Gly
        835                 840                 845

Glu Thr Glu Ala Gly Pro His Ala Phe Gly Val Glu Thr Ala Glu Lys
850                 855                 860

Val Tyr Gly Glu Tyr Tyr Asp Lys Met Phe Lys Ser Met Asn Asn Ser
865                 870                 875                 880

Tyr Lys Leu Leu Ala Lys Lys Pro Leu Glu Asp Ser Lys His Arg Val
                885                 890                 895

Leu Met Ala Ile Asn Ser Ala Lys Glu Ser Ala Lys Leu Arg Thr Gly
            900                 905                 910

Ser Ile Leu Ala Asn Tyr Ala Ser Ser Ile Leu Leu Phe Asp Gly Leu
        915                 920                 925

Pro Leu Lys Leu Asn Pro Ile Ile Arg Ser Leu Met Asp Ser Val Lys
930                 935                 940

Glu Glu Arg Asn Glu Lys Leu Gln Thr Met Ala Gly Glu Ser Val Val
945                 950                 955                 960

His Leu Ile Gln Gln Leu Leu Glu Asn Asn Lys Val Asn Val Ser Gly
                965                 970                 975

Lys Ile Val Lys Asn Leu Cys Gly Phe Leu Cys Val Asp Thr Ser Glu
            980                 985                 990

Val Pro Asp Phe Ser Val Asn Ala Glu Tyr Lys Glu Lys Ile Leu Thr
        995                 1000                1005

Leu Ile Lys Glu Ser Asn Ser Ile Ala Ala Gln Asp Asp Ile Asn
        1010                1015                1020

Leu Ala Lys Met Ser Glu Glu Ala Gln Leu Lys Arg Lys Gly Gly
        1025                1030                1035

Leu Ile Thr Leu Lys Ile Leu Phe Glu Val Leu Gly Pro Ser Ile
        1040                1045                1050

Leu Gln Lys Leu Pro Gln Leu Arg Ser Ile Leu Phe Asp Ser Leu
        1055                1060                1065

Ser Asp His Glu Asn Glu Glu Ala Ser Lys Val Asp Asn Glu Gln
        1070                1075                1080

Gly Gln Lys Ile Val Asp Ser Phe Gly Val Leu Arg Ala Leu Phe
```

-continued

```
            1085              1090              1095

Pro Phe Met Ser Asp Ser Leu Arg Ser Ser Glu Val Phe Thr Arg
    1100              1105              1110

Phe Pro Val Leu Leu Thr Phe Leu Arg Ser Asn Leu Ser Val Phe
    1115              1120              1125

Arg Tyr Ser Ala Ala Arg Thr Phe Ala Asp Leu Ala Lys Ile Ser
    1130              1135              1140

Ser Val Glu Val Met Ala Tyr Thr Ile Arg Glu Ile Leu Pro Leu
    1145              1150              1155

Met Asn Ser Ala Gly Ser Leu Ser Asp Arg Gln Gly Ser Thr Glu
    1160              1165              1170

Leu Ile Tyr His Leu Ser Leu Ser Met Glu Thr Asp Val Leu Pro
    1175              1180              1185

Tyr Val Ile Phe Leu Ile Val Pro Leu Leu Gly Arg Met Ser Asp
    1190              1195              1200

Ser Asn Glu Asp Val Arg Asn Leu Ala Thr Thr Thr Phe Ala Ser
    1205              1210              1215

Ile Ile Lys Leu Val Pro Leu Glu Ala Gly Ile Ala Asp Pro Lys
    1220              1225              1230

Gly Leu Pro Glu Glu Leu Val Ala Ser Arg Glu Arg Glu Arg Asp
    1235              1240              1245

Phe Ile Gln Gln Met Met Asp Pro Ser Lys Ala Lys Pro Phe Lys
    1250              1255              1260

Leu Pro Ile Ala Ile Lys Ala Thr Leu Arg Lys Tyr Gln Gln Asp
    1265              1270              1275

Gly Val Asn Trp Leu Ala Phe Leu Asn Lys Tyr His Leu His Gly
    1280              1285              1290

Ile Leu Cys Asp Asp Met Gly Leu Gly Lys Thr Leu Gln Thr Ile
    1295              1300              1305

Cys Ile Ile Ala Ser Asp Gln Tyr Leu Arg Lys Glu Asp Tyr Glu
    1310              1315              1320

Lys Thr Arg Ser Val Glu Ser Arg Ala Leu Pro Ser Leu Ile Ile
    1325              1330              1335

Cys Pro Pro Ser Leu Thr Gly His Trp Glu Asn Glu Phe Asp Gln
    1340              1345              1350

Tyr Ala Pro Phe Leu Lys Val Val Tyr Ala Gly Gly Pro Thr
    1355              1360              1365

Val Arg Leu Thr Leu Arg Pro Gln Leu Ser Asp Ala Asp Ile Ile
    1370              1375              1380

Val Thr Ser Tyr Asp Val Ala Arg Asn Asp Leu Ala Val Leu Asn
    1385              1390              1395

Lys Thr Glu Tyr Asn Tyr Cys Val Leu Asp Glu Gly His Ile Ile
    1400              1405              1410

Lys Asn Ser Gln Ser Lys Leu Ala Lys Ala Val Lys Glu Ile Thr
    1415              1420              1425

Ala Asn His Arg Leu Ile Leu Thr Gly Thr Pro Ile Gln Asn Asn
    1430              1435              1440

Val Leu Glu Leu Trp Ser Leu Phe Asp Phe Leu Met Pro Gly Phe
    1445              1450              1455

Leu Gly Thr Glu Lys Met Phe Gln Glu Arg Phe Ala Lys Pro Ile
    1460              1465              1470

Ala Ala Ser Arg Asn Ser Lys Thr Ser Ser Lys Glu Gln Glu Ala
    1475              1480              1485
```

```
Gly Val Leu Ala Leu Glu Ala Leu His Lys Gln Val Leu Pro Phe
    1490                1495                1500

Met Leu Arg Arg Leu Lys Glu Asp Val Leu Ser Asp Leu Pro Pro
    1505                1510                1515

Lys Ile Ile Gln Asp Tyr Tyr Cys Glu Leu Gly Asp Leu Gln Lys
    1520                1525                1530

Gln Leu Tyr Met Asp Phe Thr Lys Lys Gln Lys Asn Val Val Glu
    1535                1540                1545

Lys Asp Ile Glu Asn Ser Glu Ile Ala Asp Gly Lys Gln His Ile
    1550                1555                1560

Phe Gln Ala Leu Gln Tyr Met Arg Lys Leu Cys Asn His Pro Ala
    1565                1570                1575

Leu Val Leu Ser Pro Asn His Pro Gln Leu Ala Gln Val Gln Asp
    1580                1585                1590

Tyr Leu Lys Gln Thr Gly Leu Asp Leu His Asp Ile Ile Asn Ala
    1595                1600                1605

Pro Lys Leu Ser Ala Leu Arg Thr Leu Leu Phe Glu Cys Gly Ile
    1610                1615                1620

Gly Glu Glu Asp Ile Asp Lys Lys Ala Ser Gln Asp Gln Asn Phe
    1625                1630                1635

Pro Ile Gln Asn Val Ile Ser Gln His Arg Ala Leu Ile Phe Cys
    1640                1645                1650

Gln Leu Lys Asp Met Leu Asp Met Val Glu Asn Asp Leu Phe Lys
    1655                1660                1665

Lys Tyr Met Pro Ser Val Thr Tyr Met Arg Leu Asp Gly Ser Ile
    1670                1675                1680

Asp Pro Arg Asp Arg Gln Lys Val Val Arg Lys Phe Asn Glu Asp
    1685                1690                1695

Pro Ser Ile Asp Cys Leu Leu Leu Thr Thr Lys Val Gly Gly Leu
    1700                1705                1710

Gly Leu Asn Leu Thr Gly Ala Asp Thr Val Ile Phe Val Glu His
    1715                1720                1725

Asp Trp Asn Pro Met Asn Asp Leu Gln Ala Met Asp Arg Ala His
    1730                1735                1740

Arg Ile Gly Gln Lys Lys Val Val Asn Val Tyr Arg Ile Ile Thr
    1745                1750                1755

Lys Gly Thr Leu Glu Glu Lys Ile Met Gly Leu Gln Lys Phe Lys
    1760                1765                1770

Met Asn Ile Ala Ser Thr Val Val Asn Gln Gln Asn Ser Gly Leu
    1775                1780                1785

Ala Ser Met Asp Thr His Gln Leu Leu Asp Leu Phe Asp Pro Asp
    1790                1795                1800

Asn Val Thr Ser Gln Asp Asn Glu Glu Lys Asn Asn Gly Asp Ser
    1805                1810                1815

Gln Ala Ala Lys Gly Met Glu Asp Ile Ala Asn Glu Thr Gly Leu
    1820                1825                1830

Thr Gly Lys Ala Lys Glu Ala Leu Gly Glu Leu Lys Glu Leu Trp
    1835                1840                1845

Asp Pro Ser Gln Tyr Glu Glu Glu Tyr Asn Leu Asp Thr Phe Ile
    1850                1855                1860

Lys Thr Leu Arg
    1865
```

<210> SEQ ID NO 6
<211> LENGTH: 747
<212> TYPE: PRT
<213> ORGANISM: Homo sapiens

<400> SEQUENCE: 6

```
Met Arg Arg Ser Leu Ala Pro Ser Gln Leu Ala Lys Arg Lys Pro Glu
1               5                   10                  15

Gly Arg Ser Cys Asp Asp Glu Asp Trp Gln Pro Gly Leu Val Thr Pro
            20                  25                  30

Arg Lys Arg Lys Ser Ser Ser Glu Thr Gln Ile Gln Glu Cys Phe Leu
        35                  40                  45

Ser Pro Phe Arg Lys Pro Leu Ser Gln Leu Thr Asn Gln Pro Pro Cys
50                  55                  60

Leu Asp Ser Ser Gln His Glu Ala Phe Ile Arg Ser Ile Leu Ser Lys
65                  70                  75                  80

Pro Phe Lys Val Pro Ile Pro Asn Tyr Gln Gly Pro Leu Gly Ser Arg
                85                  90                  95

Ala Leu Gly Leu Lys Arg Ala Gly Val Arg Arg Ala Leu His Asp Pro
            100                 105                 110

Leu Glu Lys Asp Ala Leu Val Leu Tyr Glu Pro Pro Leu Ser Ala
        115                 120                 125

His Asp Gln Leu Lys Leu Asp Lys Glu Lys Leu Pro Val His Val Val
130                 135                 140

Val Asp Pro Ile Leu Ser Lys Val Leu Arg Pro His Gln Arg Glu Gly
145                 150                 155                 160

Val Lys Phe Leu Trp Glu Cys Val Thr Ser Arg Arg Ile Pro Gly Ser
                165                 170                 175

His Gly Cys Ile Met Ala Asp Glu Met Gly Leu Gly Lys Thr Leu Gln
            180                 185                 190

Cys Ile Thr Leu Met Trp Thr Leu Leu Arg Gln Ser Pro Glu Cys Lys
        195                 200                 205

Pro Glu Ile Asp Lys Ala Val Val Ser Pro Ser Leu Val Lys
210                 215                 220

Asn Trp Tyr Asn Glu Val Gly Lys Trp Leu Gly Gly Arg Ile Gln Pro
225                 230                 235                 240

Leu Ala Ile Asp Gly Gly Ser Lys Asp Glu Ile Asp Gln Lys Leu Glu
                245                 250                 255

Gly Phe Met Asn Gln Arg Gly Ala Arg Val Ser Ser Pro Ile Leu Ile
            260                 265                 270

Ile Ser Tyr Glu Thr Phe Arg Leu His Val Gly Val Leu Gln Lys Gly
        275                 280                 285

Ser Val Gly Leu Val Ile Cys Asp Glu Gly His Arg Leu Lys Asn Ser
290                 295                 300

Glu Asn Gln Thr Tyr Gln Ala Leu Asp Ser Leu Asn Thr Ser Arg Arg
305                 310                 315                 320

Val Leu Ile Ser Gly Thr Pro Ile Gln Asn Asp Leu Leu Glu Tyr Phe
                325                 330                 335

Ser Leu Val His Phe Val Asn Ser Gly Ile Leu Gly Thr Ala His Glu
            340                 345                 350

Phe Lys Lys His Phe Glu Leu Pro Ile Leu Lys Gly Arg Asp Ala Ala
        355                 360                 365

Ala Ser Glu Ala Asp Arg Gln Leu Gly Glu Glu Arg Leu Arg Glu Leu
370                 375                 380
```

-continued

```
Thr Ser Ile Val Asn Arg Cys Leu Ile Arg Arg Thr Ser Asp Ile Leu
385                 390                 395                 400

Ser Lys Tyr Leu Pro Val Lys Ile Glu Gln Val Val Cys Cys Arg Leu
            405                 410                 415

Thr Pro Leu Gln Thr Glu Leu Tyr Lys Arg Phe Leu Arg Gln Ala Lys
                420                 425                 430

Pro Ala Glu Glu Leu Leu Glu Gly Lys Met Ser Val Ser Ser Leu Ser
            435                 440                 445

Ser Ile Thr Ser Leu Lys Lys Leu Cys Asn His Pro Ala Leu Ile Tyr
450                 455                 460

Asp Lys Cys Val Glu Glu Asp Gly Phe Val Gly Ala Leu Asp Leu
465                 470                 475                 480

Phe Pro Pro Gly Tyr Ser Ser Lys Ala Leu Glu Pro Gln Leu Ser Gly
                485                 490                 495

Lys Met Leu Val Leu Asp Tyr Ile Leu Ala Val Thr Arg Ser Arg Ser
            500                 505                 510

Ser Asp Lys Val Val Leu Val Ser Asn Tyr Thr Gln Thr Leu Asp Leu
            515                 520                 525

Phe Glu Lys Leu Cys Arg Ala Arg Arg Tyr Leu Tyr Val Arg Leu Asp
530                 535                 540

Gly Thr Met Ser Ile Lys Lys Arg Ala Lys Val Val Glu Arg Phe Asn
545                 550                 555                 560

Ser Pro Ser Ser Pro Asp Phe Val Phe Met Leu Ser Ser Lys Ala Gly
                565                 570                 575

Gly Cys Gly Leu Asn Leu Ile Gly Ala Asn Arg Leu Val Met Phe Asp
            580                 585                 590

Pro Asp Trp Asn Pro Ala Asn Asp Glu Gln Ala Met Ala Arg Val Trp
            595                 600                 605

Arg Asp Gly Gln Lys Lys Thr Cys Tyr Ile Tyr Arg Leu Leu Ser Ala
610                 615                 620

Gly Thr Ile Glu Glu Lys Ile Phe Gln Arg Gln Ser His Lys Lys Ala
625                 630                 635                 640

Leu Ser Ser Cys Val Val Asp Glu Glu Gln Asp Val Glu Arg His Phe
                645                 650                 655

Ser Leu Gly Glu Leu Lys Glu Leu Phe Ile Leu Asp Glu Ala Ser Leu
            660                 665                 670

Ser Asp Thr His Asp Arg Leu His Cys Arg Arg Cys Val Asn Ser Arg
            675                 680                 685

Gln Ile Arg Pro Pro Asp Gly Ser Asp Cys Thr Ser Asp Leu Ala
690                 695                 700

Gly Trp Asn His Cys Thr Asp Lys Trp Gly Leu Arg Asp Glu Val Leu
705                 710                 715                 720

Gln Ala Ala Trp Asp Ala Ala Ser Thr Ala Ile Thr Phe Val Phe His
                725                 730                 735

Gln His Ser His Glu Glu Gln Arg Gly Leu Arg
            740                 745
```

<210> SEQ ID NO 7
<211> LENGTH: 2476
<212> TYPE: PRT
<213> ORGANISM: Mus musculus

<400> SEQUENCE: 7

Met Thr Ala Glu Pro Met Ser Gly Asn Lys Leu Ser Thr Leu Val Gln

-continued

```
1               5                   10                  15

Lys Leu His Asp Phe Leu Ala His Ser Ser Glu Ser Glu Glu Thr
            20                  25              30

Cys Ser Ser Pro Arg Leu Val Met Asn Gln Ser Thr Asp Lys Ile Cys
        35                  40              45

Gly Ser Gly Leu Asn Ser Asp Met Met Glu Asn Asn Lys Glu Glu Gly
    50                  55              60

Ala Ser Thr Ser Glu Lys Ser Arg Ser Ser Gly Ser Ser Arg Ser Lys
65                  70              75                      80

Arg Lys Pro Ser Ile Val Thr Lys Tyr Val Glu Ser Asp Asp Glu Lys
                85                  90              95

Pro Thr Asp Glu Asn Val Asn Glu Lys Ala Ala Thr Glu Asn Ser Glu
            100                 105             110

Asn Asp Ile Thr Met Gln Ser Leu Pro Lys Gly Thr Val Ile Val Gln
            115                 120             125

Pro Glu Pro Val Leu Asn Glu Asp Lys Asp Phe Lys Gly Pro Glu
        130                 135             140

Phe Arg Ser Arg Ser Lys Met Lys Ala Asp Asn Leu Ile Lys Arg Gly
145                 150                 155                     160

Glu Asp Gly Leu His Gly Ile Val Ser Cys Thr Ala Cys Gly Gln Gln
                165                 170                 175

Val Asn His Phe Gln Lys Asp Ser Ile Tyr Arg His Pro Ser Leu Lys
            180                 185                 190

Val Leu Ile Cys Lys Asn Cys Phe Lys Tyr Tyr Met Ser Asp Asp Ile
        195                 200                 205

Ser Arg Asp Ser Asp Gly Met Asp Glu Gln Cys Arg Trp Cys Ala Glu
    210                 215                 220

Gly Gly Asn Leu Ile Cys Cys Asp Phe Cys His Asn Ala Phe Cys Lys
225                 230                 235                     240

Lys Cys Ile Leu Arg Asn Leu Gly Arg Lys Glu Leu Ser Thr Ile Met
                245                 250                 255

Asp Glu Asn Asn Gln Trp Tyr Cys Tyr Ile Cys Gln Pro Glu Pro Leu
            260                 265                 270

Leu Asp Leu Val Thr Ala Cys Asn Ser Val Phe Glu Asn Leu Glu Gln
        275                 280                 285

Leu Leu Gln Gln Asn Lys Lys Ile Lys Val Asp Ser Glu Lys Thr
    290                 295                 300

Ser Lys Val Cys Asp Gln Thr Ser Lys Phe Ser Pro Lys Lys Ser Ser
305                 310                 315                     320

Ser Ser Cys Asn Gly Glu Glu Lys Lys Leu Glu Glu Ser Cys Ser Gly
                325                 330                 335

Ser Val Ser Ser Thr Tyr Ser His Ser Ala Leu Ser Val Pro Lys Glu
            340                 345                 350

Met Ile Lys Lys Thr Thr Lys Leu Ile Glu Thr Thr Ser Asn Met Asn
        355                 360                 365

Ser Ser Tyr Ile Lys Phe Leu Lys Gln Ala Ala Asp Asn Ser Glu Met
    370                 375                 380

Thr Ser Ala Met Lys Leu Cys Gln Leu Lys Ser Phe Lys Ser Val Leu
385                 390                 395                     400

Asp Asp Ile Lys Lys Ala His Leu Ala Leu Glu Glu Asp Leu Asn Ser
                405                 410                 415

Glu Ile Gln Ala Leu Asp Asp Val His Lys Glu Lys Asn Thr Lys Asp
            420                 425                 430
```

```
Leu Lys Ser Thr Asp Ala Lys Ser Glu Thr Lys Leu Gly Lys Gly Glu
            435                 440                 445

Lys Ser Tyr Ser Thr Glu Lys Arg Glu Phe Leu Lys Leu Asp Ala Arg
        450                 455                 460

Ser Ser Val Lys Ala Ile Asp Gly Glu Gln Arg Ala His Lys Ser
465                 470                 475                 480

Thr Ser Gly Glu His Lys Gly Ser Gly Arg Lys Asp Gly Ser Gln Tyr
                485                 490                 495

Glu Pro Thr Asn Thr Pro Glu Asp Leu Asp Met Asp Ile Val Ser Val
                500                 505                 510

Pro Ser Ser Val Pro Glu Asp Ile Phe Asp Ser Leu Glu Ser Ala Met
        515                 520                 525

Glu Val Gln Ser Ser Ala Asp Tyr Gln Gly Asp Gly Asn Ser Gly Thr
        530                 535                 540

Glu Pro Glu Leu Glu Ser Ser Val Lys Leu Asn Val Ser Ser Lys
545                 550                 555                 560

Asp Ser Arg Gly Asn Ile Lys Ser Lys Val Thr Ala Lys Val Arg Lys
                565                 570                 575

Glu Leu Phe Val Lys Leu Thr Pro Val Ser Leu Ser Asn Ser Pro Ile
                580                 585                 590

Lys Gly Val Asp Cys Gln Glu Val Ser Gln Glu Lys Asn Gly Arg Lys
        595                 600                 605

Ser Ser Gly Val Ala Arg Ser Ser Glu Lys Cys Arg Pro Arg Glu Glu
        610                 615                 620

Ile Ser Asp His Glu Asn Asn Val Thr Ile Leu Leu Glu Asp Ser Asp
625                 630                 635                 640

Leu Arg Arg Ser Pro Arg Val Lys Thr Thr Pro Leu Arg Arg Gln Thr
                645                 650                 655

Glu Ser Asn Pro Ala Met Ser Asn Ser Asp Glu Glu Ser Asn Gly Thr
                660                 665                 670

Met Lys Glu Lys Gln Lys Met Ser Gly Pro Ile Arg Lys Lys Asp Lys
        675                 680                 685

Arg Asn Ser Ala Asp Cys Ala Thr Asp Asn Pro Lys Pro His Lys Val
        690                 695                 700

Pro Lys Ala Lys Gln Pro Val Ile Gly Asp Gln Asn Ser Asp Ser Asp
705                 710                 715                 720

Glu Met Leu Ala Val Leu Lys Glu Ala Ser Gln Met Gly His Ser Ser
                725                 730                 735

Ser Ser Asp Thr Asp Ile Asn Glu Pro Gln Met Asn His Lys Gly Lys
                740                 745                 750

Thr Gly Lys Asp Asp Asn Gly Lys Arg Lys Arg Lys Asn Ser Thr Ser
        755                 760                 765

Gly Ser Asp Phe Asp Thr Lys Lys Gly Lys Ser Thr Glu Thr Ser Ile
        770                 775                 780

Ile Ser Lys Lys Lys Arg Gln Asn Tyr Ser Glu Ser Ser Asn Tyr Asp
785                 790                 795                 800

Ser Glu Leu Glu Arg Glu Ile Lys Thr Met Ser Arg Ile Gly Ala Ala
                805                 810                 815

Arg Lys Ser Val Pro Glu Lys Lys Glu Glu Asp Ser Ser Glu Asp Glu
                820                 825                 830

Lys Gln Gly Lys Lys Val Val Asp Asn Gly Gly His Glu Arg Ala Lys
        835                 840                 845
```

```
Thr Thr Gln Glu Gly Ser Ser Ala Asp Asp Thr Gly Asp Thr Glu Gly
    850                 855                 860

Arg Gln Gly Gly Ser Cys Ser Ile Ala Gly Gly Ser Ile Glu Lys Val
865                 870                 875                 880

Arg Ser Gly Val Glu Phe Arg Glu Met Leu Cys Lys Pro Gly Val Ser
                885                 890                 895

Ser Asp Gly Ala Glu Lys Pro Ser Val Lys Glu Asn Val Asn Ser
            900                 905                 910

Pro Glu Asp Lys Arg Val Ser Lys Thr Lys Glu Lys Thr Lys His Leu
            915                 920                 925

Arg Ser Arg Gln Ser Arg Lys Gly Lys Gly Ser Ser Asp Gly Thr
    930                 935                 940

Asp Arg Phe Pro Lys Lys Glu Gln Ser Asp Glu Ser Ser Glu Gly Glu
945                 950                 955                 960

Lys Lys Gln Ser Arg Gln Arg Pro Gly Thr Lys Gly Lys Ala Pro
                965                 970                 975

Asp Leu Lys Gly Glu Thr Leu Lys Arg Glu Gln Glu Trp Asp Ser Ser
            980                 985                 990

Ser Asp Gly Thr Glu Arg Leu Pro Glu Glu Glu Glu Ile Gly Pro Phe
    995                 1000                1005

Ser Lys Gly Ile Lys Gln Ser Lys Thr Asp Thr Ala Gly Gly Glu
    1010                1015                1020

Lys Lys Gly Lys Lys Trp Lys Asp Lys Ser Cys Glu Lys Lys Glu
    1025                1030                1035

Glu Leu Ser Asp Ser Val Asp Lys Leu Pro Gly Lys Gly Asp Ser
    1040                1045                1050

Cys Asp Ser Ser Glu Asp Lys Lys Thr Arg Asn Arg Val Ser Leu
    1055                1060                1065

Arg Glu Lys Lys Arg Phe Ser Leu Pro Ala Lys Ser Pro Gly Lys
    1070                1075                1080

Arg Pro Glu Cys Ser Ser Ser Asp Thr Glu Lys Ser Leu Lys Gly
    1085                1090                1095

Gln Cys Cys Asp Ser Thr Glu Lys Arg Pro Lys Arg Ile Asp Leu
    1100                1105                1110

Arg Glu Arg Arg Asn Ser Ser Ser Lys Arg Asn Thr Lys Glu Val
    1115                1120                1125

Lys Ser Ala Ser Ser Ser Asp Ala Glu Gly Ser Ser Glu Asp
    1130                1135                1140

Asn Lys Lys Gln Lys Lys Gln Arg Thr Ser Ala Lys Lys Thr
    1145                1150                1155

Gly Asn Thr Lys Glu Lys Lys Arg Asn Ser Leu Arg Ala Thr Pro
    1160                1165                1170

Lys Arg Lys Gln Val Asp Ile Thr Ser Ser Ser Asp Ile Gly
    1175                1180                1185

Asp Asp Asp Gln Asn Ser Ala Gly Glu Glu Ser Ser Asp Glu Gln
    1190                1195                1200

Lys Ile Lys Pro Val Thr Glu Asn Leu Val Leu Pro Ser His Thr
    1205                1210                1215

Gly Phe Cys Gln Ser Ser Gly Asp Glu Ala Leu Ser Lys Ser Val
    1220                1225                1230

Pro Ala Thr Val Asp Asp Asp Asp Asp Asn Asp Pro Glu Asn
    1235                1240                1245

Arg Ile Ala Lys Lys Met Leu Leu Glu Glu Ile Lys Ala Asn Leu
```

-continued

```
                1250                1255                1260
    Ser Ser Asp Glu Asp Gly Ser Ser Asp Glu Pro Asp Gly Gly
        1265                1270                1275
    Gly Lys Lys Arg Ile Gly Lys Gln Ser Glu Glu Ser Pro Ala Asp
        1280                1285                1290
    Asp Gly Glu Leu Arg Arg Glu Gln Leu Ala Val Asn Gln Val Asn
        1295                1300                1305
    Ser Glu Ser Asp Ser Asp Ser Glu Glu Ser Lys Lys Pro Arg Tyr
        1310                1315                1320
    Arg His Arg Leu Leu Arg His Lys Leu Thr Leu Ser Asp Gly Glu
        1325                1330                1335
    Ser Gly Glu Glu Lys Pro Thr Lys Pro Lys Glu His Lys Glu Ala
        1340                1345                1350
    Lys Gly Arg Asn Arg Arg Lys Val Ser Ser Glu Asp Ser Glu Asp
        1355                1360                1365
    Thr Asp Phe Gln Glu Ser Gly Val Ser Glu Glu Val Ser Glu Ser
        1370                1375                1380
    Glu Asp Glu Gln Arg Pro Arg Thr Arg Ser Ala Lys Lys Ala Glu
        1385                1390                1395
    Leu Glu Glu Asn Gln Arg Ser Tyr Lys Gln Lys Lys Lys Arg Arg
        1400                1405                1410
    Arg Ile Lys Val Gln Glu Asp Ser Ser Ser Glu Asn Lys Ser His
        1415                1420                1425
    Ser Glu Glu Asp Lys Lys Glu Gly Asp Glu Glu Asp Glu Glu Asp
        1430                1435                1440
    Glu Asp Glu Asp Glu Glu Asp Glu Asn Asp Asp Ser Lys Ser Pro
        1445                1450                1455
    Gly Lys Gly Arg Lys Lys Ile Arg Lys Ile Leu Lys Asp Asp Lys
        1460                1465                1470
    Leu Arg Thr Glu Thr Gln Asn Ala Leu Lys Glu Glu Glu Glu Arg
        1475                1480                1485
    Arg Lys Arg Ile Ala Glu Arg Glu Arg Glu Arg Glu Lys Leu Arg
        1490                1495                1500
    Glu Val Ile Glu Ile Glu Asp Ala Ser Pro Thr Lys Cys Pro Ile
        1505                1510                1515
    Thr Thr Lys Leu Val Leu Asp Glu Asn Glu Glu Thr Lys Glu Pro
        1520                1525                1530
    Leu Val Gln Val His Arg Asn Met Val Ile Lys Leu Lys Pro His
        1535                1540                1545
    Gln Val Asp Gly Val Gln Phe Met Trp Asp Cys Cys Cys Glu Ser
        1550                1555                1560
    Val Glu Lys Thr Lys Lys Ser Pro Gly Ser Gly Cys Ile Leu Ala
        1565                1570                1575
    His Cys Met Gly Leu Gly Lys Thr Leu Gln Val Val Ser Phe Leu
        1580                1585                1590
    His Thr Val Leu Leu Cys Asp Lys Leu Asp Phe Ser Thr Ala Leu
        1595                1600                1605
    Val Val Cys Pro Leu Asn Thr Ala Leu Asn Trp Met Asn Glu Phe
        1610                1615                1620
    Glu Lys Trp Gln Glu Gly Leu Asn Asp Asn Glu Lys Leu Glu Val
        1625                1630                1635
    Ser Glu Leu Ala Thr Val Lys Arg Pro Gln Glu Arg Ser Tyr Met
        1640                1645                1650
```

-continued

```
Leu Gln Arg Trp Gln Glu Asp Gly Gly Val Met Ile Ile Gly Tyr
    1655                1660                1665
Glu Met Tyr Arg Asn Leu Ala Gln Gly Arg Asn Val Lys Ser Arg
    1670                1675                1680
Lys Leu Lys Asp Ile Phe Asn Lys Ala Leu Val Asp Pro Gly Pro
    1685                1690                1695
Asp Phe Val Val Cys Asp Glu Gly His Ile Leu Lys Asn Glu Ala
    1700                1705                1710
Ser Ala Val Ser Lys Ala Met Asn Ser Ile Lys Ser Arg Arg Arg
    1715                1720                1725
Ile Ile Leu Thr Gly Thr Pro Leu Gln Asn Asn Leu Ile Glu Tyr
    1730                1735                1740
His Cys Met Val Asn Phe Ile Lys Glu Asn Leu Leu Gly Ser Ile
    1745                1750                1755
Lys Glu Phe Arg Asn Arg Phe Ile Asn Pro Ile Gln Asn Gly Gln
    1760                1765                1770
Cys Ala Asp Ser Thr Met Val Asp Val Arg Val Met Lys Lys Arg
    1775                1780                1785
Ala His Ile Leu Tyr Glu Met Leu Ala Gly Cys Val Gln Arg Lys
    1790                1795                1800
Asp Tyr Thr Ala Leu Thr Lys Phe Leu Pro Pro Lys His Glu Tyr
    1805                1810                1815
Val Leu Ala Val Arg Met Thr Ala Ile Gln Cys Lys Leu Tyr Gln
    1820                1825                1830
Tyr Tyr Leu Asp His Leu Thr Gly Val Gly Asn Ser Thr Glu Gly
    1835                1840                1845
Gly Arg Gly Lys Ala Gly Ala Lys Leu Phe Gln Asp Phe Gln Met
    1850                1855                1860
Leu Ser Arg Ile Trp Thr His Pro Trp Cys Leu Gln Leu Asp Tyr
    1865                1870                1875
Ile Ser Lys Glu Asn Lys Gly Tyr Phe Asp Glu Asp Ser Met Asp
    1880                1885                1890
Glu Phe Ile Ala Ser Asp Ser Asp Glu Thr Ser Lys Ser Leu Ser
    1895                1900                1905
Ser Asp Glu Lys Lys Lys Pro Lys Gly Lys Lys Gly Lys Lys Asp
    1910                1915                1920
Ser Ser Ser Ser Gly Ser Gly Ser Asp Asn Asp Val Glu Val Ile
    1925                1930                1935
Lys Val Trp Asn Ser Arg Ser Arg Gly Gly Gly Asp Gly Asn Met
    1940                1945                1950
Asp Asp Thr Gly Asn Asn Pro Ser Val Ser Leu Lys Leu Asp Glu
    1955                1960                1965
Ser Lys Thr Thr Ser Thr Ser Asn Pro Ser Ser Pro Ala Pro Asp
    1970                1975                1980
Trp Tyr Lys Asp Phe Val Thr Asp Thr Asp Ala Glu Val Leu Glu
    1985                1990                1995
His Ser Gly Lys Met Val Leu Leu Phe Glu Ile Leu Arg Met Ala
    2000                2005                2010
Glu Glu Ile Gly Asp Lys Val Leu Val Phe Ser Gln Ser Leu Ile
    2015                2020                2025
Ser Leu Asp Leu Ile Glu Asp Phe Leu Glu Leu Ala Ser Arg Glu
    2030                2035                2040
```

-continued

```
Lys Thr Glu Asp Lys Glu Lys Pro Leu Ile Tyr Lys Gly Glu Gly
    2045                2050                2055

Lys Trp Ile Arg Asn Ile Asp Tyr Tyr Arg Leu Asp Gly Ser Thr
    2060                2065                2070

Asn Ala Gln Ser Arg Lys Lys Trp Ala Glu Glu Phe Asn Asp Glu
    2075                2080                2085

Thr Asn Val Arg Gly Arg Leu Phe Ile Ile Ser Thr Lys Ala Gly
    2090                2095                2100

Ser Leu Gly Ile Asn Leu Val Ala Ala Asn Arg Val Ile Ile Phe
    2105                2110                2115

Asp Ala Ser Trp Asn Pro Ser Tyr Asp Ile Gln Ser Ile Phe Arg
    2120                2125                2130

Val Tyr Arg Phe Gly Gln Thr Lys Pro Val Tyr Val Tyr Arg Phe
    2135                2140                2145

Leu Ala Gln Gly Thr Met Glu Asp Lys Ile Tyr Asp Arg Gln Val
    2150                2155                2160

Thr Lys Gln Ser Leu Ser Phe Arg Val Val Asp Gln Gln Gln Val
    2165                2170                2175

Glu Arg His Phe Thr Met Asn Glu Leu Thr Glu Leu Tyr Thr Phe
    2180                2185                2190

Glu Pro Asp Leu Leu Asp Asp Pro Asn Ser Glu Lys Lys Lys Lys
    2195                2200                2205

Arg Asp Thr Pro Met Leu Pro Lys Asp Thr Ile Leu Ala Glu Leu
    2210                2215                2220

Leu Gln Ile His Lys Glu His Ile Val Gly Tyr His Glu His Asp
    2225                2230                2235

Ser Leu Leu Asp His Lys Glu Glu Glu Glu Leu Thr Glu Glu Glu
    2240                2245                2250

Arg Lys Ala Ala Trp Ala Glu Tyr Glu Ala Glu Lys Lys Gly Leu
    2255                2260                2265

Thr Met Arg Phe Asn Ile Pro Thr Gly Thr Asn Leu Pro Pro Val
    2270                2275                2280

Thr Phe Thr Ser Gln Thr Pro Tyr Ile Pro Phe Asn Leu Gly Ala
    2285                2290                2295

Leu Ser Ala Met Ser Asn Gln Gln Leu Glu Asp Leu Ile Asn Gln
    2300                2305                2310

Gly Arg Glu Lys Val Val Glu Ala Thr Asn Ser Met Thr Ala Val
    2315                2320                2325

Arg Ile Gln Pro Leu Glu Asp Ile Ile Ser Thr Val Trp Lys Glu
    2330                2335                2340

Asn Met Asn Leu Ser Glu Ala Gln Val Gln Ala Leu Ala Leu Ser
    2345                2350                2355

Arg Gln Ala Ser Gln Glu Leu Asp Val Lys Arg Arg Glu Ala Ile
    2360                2365                2370

Tyr Asn Asp Val Leu Thr Lys Gln Gln Met Leu Ile Asn Cys Val
    2375                2380                2385

Gln Arg Ile Leu Met Asn Arg Arg Leu Gln Gln Gln Tyr Thr Gln
    2390                2395                2400

Gln Gln Gln Gln Gln Leu Thr Tyr Gln Gln Ala Thr Leu Ser His
    2405                2410                2415

Leu Met Met Pro Lys Pro Pro Asn Leu Ile Met Thr Pro Ser Asn
    2420                2425                2430

Tyr Gln Gln Ile Asp Met Arg Gly Met Tyr Gln Ser Val Ala Gly
```

|     |     |     |     |     |     |     |     |     |     |     |     |     |     |
|-----|-----|-----|-----|-----|-----|-----|-----|-----|-----|-----|-----|-----|-----|
| 2435 | | | | | 2440 | | | | | 2445 | | | |
| Gly | Met | Gln | Pro | Pro | Pro | Leu | Gln | Arg | Ala | Pro | Pro | Thr | Val |
| | 2450 | | | | | 2455 | | | | | 2460 | | |
| Arg | Ser | Lys | Asn | Pro | Gly | Pro | Ser | Pro | Gly | Lys | Ser | Met | |
| | 2465 | | | | | 2470 | | | | | 2475 | | |